United States Patent [19]
Fishleigh et al.

[11] Patent Number: 5,773,572
[45] Date of Patent: Jun. 30, 1998

[54] FRAGMENTS OF PRION PROTEINS

[75] Inventors: Robert Vincent Fishleigh; Barry Robson, both of Cheshire; Roger Paul Mee, Manchester, all of England

[73] Assignee: Proteus Molecular Design Limited, Macclesfield, England

[21] Appl. No.: 244,701

[22] PCT Filed: Dec. 3, 1992

[86] PCT No.: PCT/GB92/02246

§ 371 Date: Jun. 2, 1994

§ 102(e) Date: Jun. 2, 1994

[87] PCT Pub. No.: WO93/11155

PCT Pub. Date: Jun. 10, 1993

[30] Foreign Application Priority Data

Dec. 3, 1991 [GB] United Kingdom ................... 9125747
Jul. 10, 1992 [GB] United Kingdom ................... 9214663

[51] Int. Cl.$^6$ ........................ C07K 14/435; C07H 21/04
[52] U.S. Cl. ........................ 530/324; 530/323; 530/326; 530/334; 536/23.5
[58] Field of Search .............................. 424/185.1, 193.1; 514/12, 13; 530/323, 324, 326; 536/23.5

[56] References Cited

FOREIGN PATENT DOCUMENTS

WO93/23432  11/1993  WIPO.

OTHER PUBLICATIONS

Cell, vol. 46, 417–428, Aug. 1986, "Scrapie and Cellular PrP Isoforms Are Encoded by the Same Chromosomal Gene", by K. Besler et al.

Proc. Natl. Acad. Sci., USA, vol. 87, pp. 2476–2480, Apr. 1990, "Two alleles of a neural protein gene linked to scrapie in sheep", by W. Goldman et al.

Journal of Molecular Recognition, vol. 4, 85–91, 1991, "Production and Characterization of Antibodies to Mouse Scrapie–Amyloid Protein Elicited by Non–carrier Linked Synthetic Peptide Immunogens", by Alessandro Di Martino et al.

Journal of Virology, Jul. 1991, pp. 3667–3675, "Molecular Location of a Species–Specific Epitope on the Hamster Scrapie Agent Protein" by D. Bolton et al.

Neurology, 1990, 40:513–517, "Scrapie–associated precursor proteins: Antigenic relationship between species and immunocytochemical localization in normal, scrapie, and Creutzfeldt–Jakob disease brains" by J. Safar, MD et al.

The Journal of Immunology, vol. 140 1188–1193, No. Feb. 1988, "Characterization of Prion Proteins with Monospecific Antisera to Synthetic Peptides", by R. Barry et al.

The Journal of Infectious Diseases, vol. 154, No. 3, Sep. 1986, "Monoclonal Antibodies to the Cellular and Scrapie Prion Proteins", by Ronald A. Barry.

Proc. Natl. Acad. Sci., vol. 88, pp. 7664–7668, Sep. 1991, "A prion–like protein from chicken brain copurifies with an acetylocholine receptor–inducing activity", by D. Harris.

Journal of Virology, vol.62, No. 5, May 1988, pp. 1558–1564, "Scrapie–Infected Murine Neuroblastoma Cells Produce Protease–Resistant Prion Proteins",by D. Butler.

Laboratory Investigation, vol. 57, No. 6, p.646, 1987, "Immuno–Gold Localization of Prion Filaments in Scrapie–Infected Hamster Brains", by Clayton A. Wiley et al.

J. gen Virol. 1986, 67, 1745–1750, "Immunoreactivity of a Synthetic Pentadecapeptide Corresponding to the N–Terminal Region of the Scrapie Prion Protein", by M. Shinagawa et al.

Cell, vol. 38, 127–134, 1984, "Purification and Structural Studies of a Major Scrapie Prion Protein" by Stanley Prusiner et al.

The Journal of immunology, vol. 147, 3568–3574, No. 10, Sep. 1991, "Epitope Mapping of the Syrian Hamster Prion Protein Utilizing Chimeric and Mutant Genes in a Vaccinia Virus Expression System", Mark Rogers et al.

*Primary Examiner*—Marian C. Knode
*Assistant Examiner*—Donna C. Wortman
*Attorney, Agent, or Firm*—Pennie & Edmonds LLP

[57] ABSTRACT

Synthetic polypeptides having at least one antigenic site of a prion protein are disclosed together methods for their use and manufacture and antibodies raised against such polypeptides. Diagnostic kits using the polypeptides and/or antibodies are also disclosed.

13 Claims, No Drawings

SEQUENCE LISTING ( 1 ) GENERAL INFORMATION:

( i i i ) NUMBER OF SEQUENCES: 67

( 2 ) INFORMATION FOR SEQ ID NO:1:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=X
            / note= "X may be absent or present independently
            of Y and denotes one or more amino acid(s)"

( i x ) FEATURE:
        ( A ) NAME/KEY: Modified-site
        ( B ) LOCATION: 33
        ( D ) OTHER INFORMATION: /label=Y
            / note= "Y may be absent or present independently
            of X and denotes one or more amino acid(s)

( x i ) SEQUENCE DESCRIPTION: SEQ ID NO:1:

Xaa Met Lys His Val Ala Gly Ala Ala Ala Ala Gly Ala Val Val Gly
1               5                   10                  15

Gly Leu Gly Gly Tyr Met Leu Gly Ser Ala Met Ser Arg Pro Leu Ile
            20                  25                  30

Xaa ( 2 ) INFORMATION FOR SEQ ID NO:2:

( i ) SEQUENCE CHARACTERISTICS:
    ( A ) LENGTH: 33 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=X
        / note= "X may be absent or present independently
        of Y and denotes one or more amino acid(s)"

( i x ) FEATURE:
    ( A ) NAME/KEY: Modified-site
    ( B ) LOCATION: 33
    ( D ) OTHER INFORMATION: /label=Y
        / note= "Y may be absent or present independently
        of X and denotes one or more amino acid(s)"

( x i ) SEQUENCE DESCRIPTION: SEQ ID NO:2:

Xaa Met Lys His Met Ala Gly Ala Ala Ala Ala Gly Ala Val Val Gly
1               5                   10                  15

Gly Leu Gly Gly Tyr Met Leu Gly Ser Ala Met Ser Arg Pro Ile Ile
            20                  25                  30

Xaa ( 2 ) INFORMATION FOR SEQ ID NO:3:

( i ) SEQUENCE CHARACTERISTICS:
    ( A ) LENGTH: 19 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=X
        / note= "X may be absent or present independently
        of Y and denotes one or more amino acid(s)"

( i x ) FEATURE:
    ( A ) NAME/KEY: Modified-site
    ( B ) LOCATION: 19
    ( D ) OTHER INFORMATION: /label=Y
        / note= "Y may be absent or present independently
        of X and denotes one or more amino acid(s)"

( x i ) SEQUENCE DESCRIPTION: SEQ ID NO:3:

Xaa His Val Ala Gly Ala Ala Ala Ala Gly Ala Val Val Gly Gly Leu
1               5                   10                  15

Gly Gly Xaa ( 2 ) INFORMATION FOR SEQ ID NO:4:

( i ) SEQUENCE CHARACTERISTICS:
    ( A ) LENGTH: 19 amino acids (B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=X
/ note= "Y may be absent or present independently of X and denotes one or more amino acid(s)"

(ix) FEATURE:
(A) NAME/KEY: Modified-site
(B) LOCATION: 19
(D) OTHER INFORMATION: /label=Y
/ note= "Y may be absent or present independently of X and denotes one or more amino acid(s)"

(xi) SEQUENCE DESCRIPTION: SEQ ID NO:4:

Xaa Gly Gly Leu Gly Gly Tyr Met Leu Gly Ser Ala Met Ser Arg Pro
1               5                       10                      15
Leu Ile Xaa (2) INFORMATION FOR SEQ ID NO:5:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=X
/ note= "X may be absent or present independently X of Y and denotes one or more amino acid(s)"

(ix) FEATURE:
(A) NAME/KEY: Modified-site
(B) LOCATION: 19
(D) OTHER INFORMATION: /label=Y
/ note= "Y may be absent or present independently of X and denotes one or more amino acid(s)"

(xi) SEQUENCE DESCRIPTION: SEQ ID NO:5:

Xaa His Met Ala Gly Ala Ala Ala Ala Gly Ala Val Val Gly Gly Leu
1               5                       10                      15
Gly Gly Xaa (2) INFORMATION FOR SEQ ID NO:6:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=X
/ note= "X may be absent or present independently of Y and denotes one or more amino acid(s)"

(ix) FEATURE:
(A) NAME/KEY: Modified-site
(B) LOCATION: 19
(D) OTHER INFORMATION: /label=Y / note= "Y may be absent or present independently
of X and denotes one or more amino acid(s)"

( x i ) SEQUENCE DESCRIPTION: SEQ ID NO:6:

| Xaa | Gly | Gly | Leu | Gly | Gly | Tyr | Met | Leu | Gly | Ser | Ala | Met | Ser | Arg | Pro |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Ile  Ile  Xaa ( 2 ) INFORMATION FOR SEQ ID NO:7:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=X
            / note= "X may be absent or present independently
            of Y and denotes one or more amino acid(s)"

( i x ) FEATURE:
        ( A ) NAME/KEY: Modified-site
        ( B ) LOCATION: 31
        ( D ) OTHER INFORMATION: /label=Y
            / note= "Y may be absent or present independently
            of X and denotes one or more amino acid(s)"

( x i ) SEQUENCE DESCRIPTION: SEQ ID NO:7:

| Xaa | Ser | Ala | Met | Ser | Arg | Pro | Leu | Ile | His | Phe | Gly | Ser | Asp | Tyr | Glu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Arg | Tyr | Tyr | Arg | Glu | Asn | Met | His | Arg | Tyr | Pro | Asn | Gln | Xaa |
|-----|-----|-----|-----|-----|-----|-----|-----|-----|-----|-----|-----|-----|-----|-----|
|     |     |     | 20  |     |     |     |     | 25  |     |     |     |     | 30  |     |

( 2 ) INFORMATION FOR SEQ ID NO:8:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=X
            / note= "X may be absent or present independently
            of Y and denotes one or more amino acid(s)"

( i x ) FEATURE:
        ( A ) NAME/KEY: Modified-site
        ( B ) LOCATION: 31
        ( D ) OTHER INFORMATION: /label=Y
            / note= "Y may be absent or present independently
            of X and denotes one or more amino acid(s)"

( x i ) SEQUENCE DESCRIPTION: SEQ ID NO:8:

| Xaa | Ser | Ala | Met | Ser | Arg | Pro | Leu | Ile | His | Phe | Gly | Asn | Asp | Tyr | Glu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Arg | Tyr | Tyr | Arg | Glu | Asn | Met | Tyr | Arg | Tyr | Pro | Asn | Gln | Xaa |
|-----|-----|-----|-----|-----|-----|-----|-----|-----|-----|-----|-----|-----|-----|-----|
|     |     |     | 20  |     |     |     |     | 25  |     |     |     |     | 30  |     |

( 2 ) INFORMATION FOR SEQ ID NO:9:

( i ) SEQUENCE CHARACTERISTICS:

(A) LENGTH: 31 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=X
/ note= "X may be absent or present independently of Y and denotes one or more amino acid(s)"

(ix) FEATURE:
(A) NAME/KEY: Modified-site
(B) LOCATION: 31
(D) OTHER INFORMATION: /label=Y
/ note= "Y may be absent or present independently of X and denotes one or more amino acid(s)"

(xi) SEQUENCE DESCRIPTION: SEQ ID NO:9:

Xaa Ser Ala Met Ser Arg Pro Ile Ile His Phe Gly Ser Asp Tyr Glu
1               5                   10                  15
Asp Arg Tyr Tyr Arg Glu Asn Met His Arg Tyr Pro Asn Gln Xaa
            20                  25                  30

(2) INFORMATION FOR SEQ ID NO:10:

(i) SEQUENCE CHARACTERISTICS:
(A) LENGTH: 25 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=X
/ note= "X may be absent or present independently of Y and denotes one or more amino acid(s)"

(ix) FEATURE:
(A) NAME/KEY: Modified-site
(B) LOCATION: 25
(D) OTHER INFORMATION: /label=Y
/ note= "Y may be absent or present independently of X and denotes one or more amino acid(s)"

(xi) SEQUENCE DESCRIPTION: SEQ ID NO:10:

Xaa Ser Ala Met Ser Arg Pro Leu Ile His Phe Gly Ser Asp Tyr Glu
1               5                   10                  15
Asp Arg Tyr Tyr Arg Glu Asn Met Xaa
            20                  25

(2) INFORMATION FOR SEQ ID NO:11:

(i) SEQUENCE CHARACTERISTICS:
(A) LENGTH: 25 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=X
/ note= "X may be absent or present independently of Y and denotes one or more amino acid(s)"

( i x ) FEATURE:
  ( A ) NAME/KEY: Modified-site
  ( B ) LOCATION: 25
  ( D ) OTHER INFORMATION: /label=Y
    / note= "Y may be absent or present independently
    of X and denotes one or more amino acid(s)"

( x i ) SEQUENCE DESCRIPTION: SEQ ID NO:11:

| Xaa | Ser | Ala | Met | Ser | Arg | Pro | Leu | Ile | His | Phe | Gly | Asn | Asp | Tyr | Glu |
|---|---|---|---|---|---|---|---|---|---|---|---|---|---|---|---|
| 1 | | | | 5 | | | | | 10 | | | | | | 15 |
| Asp | Arg | Tyr | Tyr | Arg | Glu | Asn | Met | Xaa | | | | | | | |
| | | | 20 | | | | | 25 | | | | | | | |

( 2 ) INFORMATION FOR SEQ ID NO:12:

( i ) SEQUENCE CHARACTERISTICS:
  ( A ) LENGTH: 25 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /label=X
    / note= "X may be absent or present independently
    of Y and denotes one or more amino acid(s)"

( i x ) FEATURE:
  ( A ) NAME/KEY: Modified-site
  ( B ) LOCATION: 25
  ( D ) OTHER INFORMATION: /label=Y
    / note= "Y may be absent or present independently
    of X and denotes one or more amino acid(s)"

( x i ) SEQUENCE DESCRIPTION: SEQ ID NO:12:

| Xaa | Ser | Ala | Met | Ser | Arg | Pro | Ile | Ile | His | Phe | Gly | Ser | Asp | Tyr | Glu |
|---|---|---|---|---|---|---|---|---|---|---|---|---|---|---|---|
| 1 | | | | 5 | | | | | 10 | | | | | | 15 |
| Asp | Arg | Tyr | Tyr | Arg | Glu | Asn | Met | Xaa | | | | | | | |
| | | | 20 | | | | | 25 | | | | | | | |

( 2 ) INFORMATION FOR SEQ ID NO:13:

( i ) SEQUENCE CHARACTERISTICS:
  ( A ) LENGTH: 31 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /label=X
    / note= "X may be absent or present independently
    of Y and denotes one or more amino acid(s)"

( i x ) FEATURE:
  ( A ) NAME/KEY: Modified-site
  ( B ) LOCATION: 31
  ( D ) OTHER INFORMATION: /label=Y
    / note= "Y may be absent or present independently
    of X and denotes one or more amino acid(s)"

( x i ) SEQUENCE DESCRIPTION: SEQ ID NO:13:

| Xaa | Asn | Met | His | Arg | Tyr | Pro | Asn | Gln | Val | Tyr | Tyr | Arg | Pro | Val | Asp |
|---|---|---|---|---|---|---|---|---|---|---|---|---|---|---|---|
| 1 | | | | 5 | | | | | 10 | | | | | | 15 |
| Gln | Tyr | Ser | Asn | Gln | Asn | Asn | Phe | Val | His | Asp | Cys | Val | Asn | Xaa | |
| | | | 20 | | | | | 25 | | | | | 30 | | |

( 2 ) INFORMATION FOR SEQ ID NO:14:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=X
            / note= "X may be absent or present independently
            of Y and denotes one or more amino acid(s)"

( i x ) FEATURE:
        ( A ) NAME/KEY: Modified-site
        ( B ) LOCATION: 31
        ( D ) OTHER INFORMATION: /label=Y
            / note= "Y may be absent or present independently
            of X and denotes one or more amino acid(s)"

( x i ) SEQUENCE DESCRIPTION: SEQ ID NO:14:

```
Xaa  Asn  Met  Tyr  Arg  Tyr  Pro  Asn  Gln  Val  Tyr  Tyr  Arg  Pro  Val  Asp
 1                   5                        10                       15
Arg  Tyr  Ser  Asn  Gln  Asn  Asn  Phe  Val  His  Asp  Cys  Val  Asn  Xaa
               20                       25                       30
```

( 2 ) INFORMATION FOR SEQ ID NO:15:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=X
            / note= "X may be absent or present independently
            of Y and denotes one or more amino acid(s)"

( i x ) FEATURE:
        ( A ) NAME/KEY: Modified-site
        ( B ) LOCATION: 31
        ( D ) OTHER INFORMATION: /label=Y
            / note= "Y may be absent or present independently
            of X and denotes one or more amino acid(s)"

( x i ) SEQUENCE DESCRIPTION: SEQ ID NO:15:

```
Xaa  Asn  Met  His  Arg  Tyr  Pro  Asn  Gln  Val  Tyr  Tyr  Arg  Pro  Met  Asp
 1                   5                        10                       15
Glu  Tyr  Ser  Asn  Gln  Asn  Asn  Phe  Val  His  Asp  Cys  Val  Asn  Xaa
               20                       25                       30
```

( 2 ) INFORMATION FOR SEQ ID NO:16:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site (B) LOCATION: 1
(D) OTHER INFORMATION: /label=X
/ note= "X may be absent or present independently
of Y and denotes one or more amino acid(s)"

(ix) FEATURE:
(A) NAME/KEY: Modified-site
(B) LOCATION: 28
(D) OTHER INFORMATION: /label=Y
/ note= "Y may be absent or present independently
of X and denotes one or more amino acid(s)"

(xi) SEQUENCE DESCRIPTION: SEQ ID NO:16:

```
Xaa  Arg  Tyr  Pro  Asn  Gln  Val  Tyr  Tyr  Arg  Pro  Val  Asp  Gln  Tyr  Ser
1                  5                          10                         15

Asn  Gln  Asn  Asn  Phe  Val  His  Asp  Cys  Val  Asn  Xaa
                    20                      25
```

(2) INFORMATION FOR SEQ ID NO:17:

(i) SEQUENCE CHARACTERISTICS:
(A) LENGTH: 28 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=X
/ note= "X may be absent or present independently
of Y and denotes one or more amino acid(s)"

(ix) FEATURE:
(A) NAME/KEY: Modified-site
(B) LOCATION: 28
(D) OTHER INFORMATION: /label=Y
/ note= "Y may be absent or present independently
of X and denotes one or more amino acid(s) "

(xi) SEQUENCE DESCRIPTION: SEQ ID NO:17:

```
Xaa  Arg  Tyr  Pro  Asn  Gln  Val  Tyr  Tyr  Arg  Pro  Val  Asp  Arg  Tyr  Ser
1                  5                          10                         15

Asn  Gln  Asn  Asn  Phe  Val  His  Asp  Cys  Val  Asn  Xaa
                    20                      25
```

(2) INFORMATION FOR SEQ ID NO:18:

(i) SEQUENCE CHARACTERISTICS:
(A) LENGTH: 28 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=X
/ note= "X may be absent or present independently
of Y and denotes one or more amino acid(s)"

(ix) FEATURE:
(A) NAME/KEY: Modified-site
(B) LOCATION: 28
(D) OTHER INFORMATION: /label=Y
/ note= "Y may be absent or present independently
of X and denotes one or more amino acid(s)"

(xi) SEQUENCE DESCRIPTION: SEQ ID NO:18:

-continued

```
Xaa Arg Tyr Pro Asn Gln Val Tyr Tyr Arg Pro Met Asp Glu Tyr Ser
 1               5                  10                  15

Asn Gln Asn Asn Phe Val His Asp Cys Val Asn Xaa
             20              25
```

( 2 ) INFORMATION FOR SEQ ID NO:19:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=X
            / note= "X may be absent or present independently
            of Y and denotes one or more amino acid(s)"

( i x ) FEATURE:
        ( A ) NAME/KEY: Modified-site
        ( B ) LOCATION: 31
        ( D ) OTHER INFORMATION: /label=Y
            / note= "Y may be absent or present independently
            of X and denotes one or more amino acid(s)"

( x i ) SEQUENCE DESCRIPTION: SEQ ID NO:19:

```
Xaa Tyr Tyr Gln Arg Gly Ala Ser Val Ile Leu Phe Ser Ser Pro Pro
 1               5                  10                  15

Val Ile Leu Leu Ile Ser Phe Leu Ile Phe Leu Ile Val Gly Xaa
             20              25                  30
```

( 2 ) INFORMATION FOR SEQ ID NO:20:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=X
            / note= "X may be absent or present independently
            of Y and denotes one or more amino acid(s)"

( i x ) FEATURE:
        ( A ) NAME/KEY: Modified-site
        ( B ) LOCATION: 31
        ( D ) OTHER INFORMATION: /label=Y
            / note= "Y may be absent or present independently
            of X and denotes one or more amino acid(s)"

( x i ) SEQUENCE DESCRIPTION: SEQ ID NO:20:

```
Xaa Tyr Tyr Gln Arg Gly Ser Ser Met Val Leu Phe Ser Ser Pro Pro
 1               5                  10                  15

Val Ile Leu Leu Ile Ser Phe Leu Ile Phe Leu Ile Val Gly Xaa
             20              25                  30
```

( 2 ) INFORMATION FOR SEQ ID NO:21:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=X
        / note= "X may be absent or present independently of Y and denotes one or more amino acid(s)"

( i x ) FEATURE:
    ( A ) NAME/KEY: Modified-site
    ( B ) LOCATION: 19
    ( D ) OTHER INFORMATION: /label=Y
        / note= "Y may be absent or present independently of X and denotes one or more amino acid(s)"

( x i ) SEQUENCE DESCRIPTION: SEQ ID NO:21:

```
Xaa  Gly  Ala  Ser  Val  Ile  Leu  Phe  Ser  Ser  Pro  Pro  Val  Ile  Leu  Leu
 1                   5                        10                       15
Ile  Ser  Xaa
```

( 2 ) INFORMATION FOR SEQ ID NO:22:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=X
            / note= "X may be absent or present independently of Y and denotes one or more amino acid(s)"

( i x ) FEATURE:
        ( A ) NAME/KEY: Modified-site
        ( B ) LOCATION: 19
        ( D ) OTHER INFORMATION: /label=Y
            / note= "Y may be absent or present independently of X and denotes one or more amino acid(s)"

( x i ) SEQUENCE DESCRIPTION: SEQ ID NO:22:

```
Xaa  Gly  Ser  Ser  Met  Val  Leu  Phe  Ser  Ser  Pro  Pro  Val  Ile  Leu  Leu
 1                   5                        10                       15
Ile  Ser  Xaa
```

( 2 ) INFORMATION FOR SEQ ID NO:23:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=X
            / note= "X may be absent or present independently of Y and denotes one or more amino acid(s)"

( i x ) FEATURE:
        ( A ) NAME/KEY: Modified-site
        ( B ) LOCATION: 33
        ( D ) OTHER INFORMATION: /label=Y
            / note= "Y may be absent or present independently of X and denotes one or more amino acid(s)"

(xi) SEQUENCE DESCRIPTION: SEQ ID NO:23:

Xaa Pro Gly Gly Gly Trp Asn Thr Gly Gly Ser Arg Tyr Pro Gly Gln
1               5                   10                  15

Gly Ser Pro Gly Gly Asn Arg Tyr Pro Pro Gln Gly Gly Gly Trp
            20                  25                  30

Xaa (2) INFORMATION FOR SEQ ID NO:24:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=X
            / note= "X may be absent or present independently
            of Y and denotes one or more amino acid(s)"

(ix) FEATURE:
        (A) NAME/KEY: Modified-site
        (B) LOCATION: 18
        (D) OTHER INFORMATION: /label=Y
            / note= "Y may be absent or present independently
            of X and denotes one or more amino acid(s)"

(xi) SEQUENCE DESCRIPTION: SEQ ID NO:24:

Xaa Gly Gly Gly Trp Gly Gln Pro His Gly Gly Trp Gly Gln Pro
1               5                   10                  15

His Xaa (2) INFORMATION FOR SEQ ID NO:25:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=X
            / note= "X may be absent or present independently
            of Y and denotes one or more amino acid(s)

(ix) FEATURE:
        (A) NAME/KEY: Modified-site
        (B) LOCATION: 30
        (D) OTHER INFORMATION: /label=Y
            / note= "Y may be absent or present independently
            of X and denotes one or more amino acid(s)"

(xi) SEQUENCE DESCRIPTION: SEQ ID NO:25:

Xaa Gly Gly Gly Trp Gly Gln Gly Gly Thr His Gly Gln Trp Asn Lys
1               5                   10                  15

Pro Ser Lys Pro Lys Thr Asn Met Lys His Val Ala Gly Xaa
            20                  25                  30

(2) INFORMATION FOR SEQ ID NO:26:

(i) SEQUENCE CHARACTERISTICS:

(A) LENGTH: 33 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=X
/ note= "X may be absent or present independently of Y and denotes one or more amino acid(s)"

(ix) FEATURE:
(A) NAME/KEY: Modified-site
(B) LOCATION: 33
(D) OTHER INFORMATION: /label=Y
/ note= "Y may be absent or present independently of X and denotes one or more amino acid(s)"

(xi) SEQUENCE DESCRIPTION: SEQ ID NO:26:

| Xaa | Pro | Gly | Gly | Gly | Trp | Asn | Thr | Gly | Gly | Ser | Arg | Tyr | Pro | Gly | Gln |
|---|---|---|---|---|---|---|---|---|---|---|---|---|---|---|---|
| 1 | | | | 5 | | | | | 10 | | | | | | 15 |

| Gly | Ser | Pro | Gly | Gly | Asn | Arg | Tyr | Pro | Pro | Gln | Gly | Gly | Gly | Trp |
|---|---|---|---|---|---|---|---|---|---|---|---|---|---|---|
| | | | 20 | | | | | 25 | | | | | 30 | |

Xaa (2) INFORMATION FOR SEQ ID NO:27:

(i) SEQUENCE CHARACTERISTICS:
(A) LENGTH: 18 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=X
/ note= "X may be absent or present independently of Y and denotes one or more amino acid(s)"

(ix) FEATURE:
(A) NAME/KEY: Modified-site
(B) LOCATION: 18
(D) OTHER INFORMATION: /label=Y
/ note= "Y may be absent or present independently of X and denotes one or more amino acid(s)"

(xi) SEQUENCE DESCRIPTION: SEQ ID NO:27:

| Xaa | Gly | Gly | Gly | Trp | Gly | Gln | Pro | His | Gly | Gly | Gly | Trp | Gly | Gln | Pro |
|---|---|---|---|---|---|---|---|---|---|---|---|---|---|---|---|
| 1 | | | | 5 | | | | | 10 | | | | | | 15 |

His Xaa (2) INFORMATION FOR SEQ ID NO:28:

(i) SEQUENCE CHARACTERISTICS:
(A) LENGTH: 30 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=X
/ note= "X may be absent or present independently of Y and denotes one or more amino acid(s)"

( i x ) FEATURE:
  ( A ) NAME/KEY: Modified-site
  ( B ) LOCATION: 30
  ( D ) OTHER INFORMATION: /label=Y
    / note= "Y may be absent or present independently
    of X and denotes one or more amino acid(s)"

( x i ) SEQUENCE DESCRIPTION: SEQ ID NO:28:

| Xaa | Gly | Gly | Gly | Trp | Gly | Gln | Gly | Gly | Ser | His | Ser | Gln | Trp | Asn | Lys |
|---|---|---|---|---|---|---|---|---|---|---|---|---|---|---|---|
| 1 | | | | 5 | | | | | 10 | | | | | | 15 |

| Pro | Ser | Lys | Pro | Lys | Thr | Asn | Met | Lys | His | Val | Ala | Gly | Xaa |
|---|---|---|---|---|---|---|---|---|---|---|---|---|---|
| | | | 20 | | | | 25 | | | | | 30 | |

( 2 ) INFORMATION FOR SEQ ID NO:29:

( i ) SEQUENCE CHARACTERISTICS:
    ( A ) LENGTH: 33 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=X
      / note= "X may be absent or present independently
      of Y and denotes one or more amino acid(s)"

( i x ) FEATURE:
    ( A ) NAME/KEY: Modified-site
    ( B ) LOCATION: 33
    ( D ) OTHER INFORMATION: /label=Y
      / note= "Y may be absent or present independently
      of X and denotes one or more amino acid(s) "

( x i ) SEQUENCE DESCRIPTION: SEQ ID NO:29:

| Xaa | Pro | Gly | Gly | Gly | Trp | Asn | Thr | Gly | Gly | Ser | Arg | Tyr | Pro | Gly | Gln |
|---|---|---|---|---|---|---|---|---|---|---|---|---|---|---|---|
| 1 | | | | 5 | | | | | 10 | | | | | | 15 |

| Gly | Ser | Pro | Gly | Gly | Asn | Arg | Tyr | Pro | Pro | Gln | Gly | Gly | Gly | Gly | Trp |
|---|---|---|---|---|---|---|---|---|---|---|---|---|---|---|---|
| | | | 20 | | | | 25 | | | | | 30 | | | |

Xaa ( 2 ) INFORMATION FOR SEQ ID NO:30:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=X
      / note= "X is absent or present independently of Y
      and denotes one or more amino acid(s)"

( i x ) FEATURE:
    ( A ) NAME/KEY: Modified-site
    ( B ) LOCATION: 18
    ( D ) OTHER INFORMATION: /label=Y
      / note= "Y may be absent or present independently
      of X and denotes one or more amino acid(s)"

( x i ) SEQUENCE DESCRIPTION: SEQ ID NO:30:

| Xaa | Gly | Gly | Gly | Trp | Gly | Gln | Pro | His | Gly | Gly | Gly | Trp | Gly | Gln | Pro |
|---|---|---|---|---|---|---|---|---|---|---|---|---|---|---|---|
| 1 | | | | 5 | | | | | 10 | | | | | | 15 |

His Xaa (2) INFORMATION FOR SEQ ID NO:31:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=X
            / note= "X may be absent or present independently
            of Y and denotes one or more amino acid(s)"

(ix) FEATURE:
        (A) NAME/KEY: Modified-site
        (B) LOCATION: 31
        (D) OTHER INFORMATION: /label=Y
            / note= "Y may be absent or present independently
            of X and denotes one or more amino acid(s)"

(xi) SEQUENCE DESCRIPTION: SEQ ID NO:31:

Xaa Gly Gly Gly Trp Gly Gln Gly Gly Gly Thr His Ser Gln Trp Asn
1               5                   10                  15

Lys Pro Ser Lys Pro Lys Thr Asn Met Lys His Met Ala Gly Xaa
            20                  25                  30

(2) INFORMATION FOR SEQ ID NO:32:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=X
            / note= "X may be absent or present independently
            of Y and denotes one or more amino acid(s)"

(ix) FEATURE:
        (A) NAME/KEY: Modified-site
        (B) LOCATION: 33
        (D) OTHER INFORMATION: /label=Y
            / note= "Y may be absent or present independently
            of X and denotes one or more amino acid(s)"

(xi) SEQUENCE DESCRIPTION: SEQ ID NO:32:

Xaa Asn Phe Val His Asp Cys Val Asn Ile Thr Val Lys Glu His Thr
1               5                   10                  15

Val Thr Thr Thr Thr Lys Gly Glu Asn Phe Thr Glu Thr Asp Ile Lys
            20                  25                  30

Xaa (2) INFORMATION FOR SEQ ID NO:33:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /label=X
        / note= "X may be absent or present independently
        of Y and denotes one or more amino acid(s)"

(ix) FEATURE:
    (A) NAME/KEY: Modified-site
    (B) LOCATION: 22
    (D) OTHER INFORMATION: /label=Y
        / note= "Y may be absent or present independently
        of X and denotes one or more amino acid(s)"

(xi) SEQUENCE DESCRIPTION: SEQ ID NO:33:

```
Xaa  Met  Cys  Ile  Thr  Gln  Tyr  Gln  Arg  Glu  Ser  Gln  Ala  Tyr  Tyr  Gln
1                  5                        10                       15

Arg  Gly  Ala  Ser  Val  Xaa
               20
```

(2) INFORMATION FOR SEQ ID NO:34:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=X
            / note= "X may be absent or present independently
            of Y and denotes one or more amino acid(s)"

(ix) FEATURE:
        (A) NAME/KEY: Modified-site
        (B) LOCATION: 33
        (D) OTHER INFORMATION: /label=Y
            / note= "Y is absent or present independently of X
            and denotes one or more amino acid(s)"

(xi) SEQUENCE DESCRIPTION: SEQ ID NO:34:

```
Xaa  Asn  Phe  Val  His  Asp  Cys  Val  Asn  Ile  Thr  Val  Lys  Gln  His  Thr
1                  5                        10                       15

Val  Thr  Thr  Thr  Thr  Lys  Gly  Glu  Asn  Phe  Thr  Glu  Thr  Asp  Ile  Lys
               20                        25                       30

Xaa
```

(2) INFORMATION FOR SEQ ID NO:35:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=X
            / note= "X may be absent or present independently
            of Y and denotes one or more amino acid(s)"

(ix) FEATURE:
        (A) NAME/KEY: Modified-site
        (B) LOCATION: 22

(D) OTHER INFORMATION: /label=Y
/ note= "Y may be absent or present independently
of X and denotes one or more amino acid(s)"

(xi) SEQUENCE DESCRIPTION: SEQ ID NO:35:

Xaa Met Cys Ile Thr Gln Tyr Gln Arg Glu Ser Gln Ala Tyr Tyr Gln
1               5                   10                  15

Arg Gly Ala Ser Val Xaa
            20

(2) INFORMATION FOR SEQ ID NO:36:

(i) SEQUENCE CHARACTERISTICS:
    (A) LENGTH: 33 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /label=X
        / note= "X may be absent or present independently
        of Y and denotes one or amino acid(s)"

(ix) FEATURE:
    (A) NAME/KEY: Modified-site
    (B) LOCATION: 33
    (D) OTHER INFORMATION: /label=Y
        / note= "Y may be absent or present independently
        of X and denotes one or more amino acid(s)"

(xi) SEQUENCE DESCRIPTION: SEQ ID NO:36:

Xaa Asn Phe Val His Asp Cys Val Asn Ile Thr Ile Lys Gln His Thr
1               5                   10                  15

Val Thr Thr Thr Thr Lys Gly Glu Asn Phe Thr Glu Thr Asp Val Lys
            20                  25                  30

Xaa (2) INFORMATION FOR SEQ ID NO:37:

(i) SEQUENCE CHARACTERISTICS:
    (A) LENGTH: 22 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /label=X
        / note= "X may be absent or present independently
        of Y and denotes one or more amino acid(s)"

(ix) FEATURE:
    (A) NAME/KEY: Modified-site
    (B) LOCATION: 22
    (D) OTHER INFORMATION: /label=Y
        / note= "Y may be absent or present independently
        of X and denotes one or more amino acid(s)"

(xi) SEQUENCE DESCRIPTION: SEQ ID NO:37:

Xaa Met Cys Ile Thr Gln Tyr Glu Arg Glu Ser Gln Ala Tyr Tyr Gln
1               5                   10                  15

Arg Gly Ser Ser Met Xaa
            20

( 2 ) INFORMATION FOR SEQ ID NO:38:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:38:

```
Gly  Gly  Gly  Gly  Gly
1                    5
```

( 2 ) INFORMATION FOR SEQ ID NO:39:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:39:

```
Gly  Pro  Gly  Pro  Gly  Pro
1                    5
```

( 2 ) INFORMATION FOR SEQ ID NO:40:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:40:

```
Gly  Ser  Ala  Gly  Ser  Gly  Ala
1                    5
```

( 2 ) INFORMATION FOR SEQ ID NO:41:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:41:

```
Ala  Met  Ser  Arg  Pro  Leu  Ile  His  Phe  Gly  Ser  Asp  Tyr  Glu  Asp  Arg
1                    5                         10                          15

Tyr  Tyr  Arg  Glu  Asn  Met  His  Arg  Gly  Cys
                20                        25
```

( 2 ) INFORMATION FOR SEQ ID NO:42:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:42:

```
         Ser  Ala  Met  Ser  Arg  Pro  Leu  Ile  His  Phe  Gly  Asn  Asp  Tyr  Glu  Asp
         1                   5                        10                       15

Arg  Tyr  Tyr  Gly  Cys
                         20
```

( 2 ) INFORMATION FOR SEQ ID NO:43:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:43:

```
         Ser  Ala  Met  Ser  Arg  Pro  Leu  Ile  His  Phe  Gly  Ser  Asp  Tyr  Glu  Asp
         1                   5                        10                       15

Arg  Tyr  Tyr  Gly  Cys
                         20
```

( 2 ) INFORMATION FOR SEQ ID NO:44:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:44:

```
         Asn  Met  Tyr  Arg  Tyr  Pro  Asn  Gln  Val  Tyr  Tyr  Arg  Pro  Val  Asp  Arg
         1                   5                        10                       15

Tyr  Ser  Asn  Gln  Asn  Asn  Phe  Val  His  Gly  Cys
                         20                        25
```

( 2 ) INFORMATION FOR SEQ ID NO:45:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:45:

```
         Asn  Met  His  Arg  Tyr  Pro  Asn  Gln  Val  Tyr  Tyr  Arg  Pro  Val  Asp  Gln
         1                   5                        10                       15

Tyr  Ser  Asn  Gln  Asn  Asn  Phe  Val  His  Gly  Cys
                         20                        25
```

( 2 ) INFORMATION FOR SEQ ID NO:46:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:46:

```
         Gly  Gln  Pro  His  Gly  Gly  Gly  Trp  Gly  Gln  Pro  His  Gly  Gly  Gly  Trp
         1                   5                        10                       15

Gly  Gln  Pro  His  Gly  Gly  Gly  Trp  Gly  Cys
```

20                              25

(2) INFORMATION FOR SEQ ID NO:47:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:47:

Gly Gln Gly Gly Ser His Ser Gln Trp Asn Lys Pro Ser Lys Pro Lys
1               5                   10                  15
Thr Asn Met Lys His Val Gly Cys
            20

(2) INFORMATION FOR SEQ ID NO:48:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:48:

Cys Ile Thr Gln Tyr Gln Arg Glu Ser Gln Ala Tyr Tyr Gln Arg
1               5                   10                  15

(2) INFORMATION FOR SEQ ID NO:49:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:49:

Gly Gly Trp Asn Thr Gly Gly Ser Arg Tyr Pro Gly Gln Gly Ser Pro
1               5                   10                  15
Gly Gly Asn Arg Tyr Pro Pro Gln Gly Gly Gly Cys
            20                  25

(2) INFORMATION FOR SEQ ID NO:50:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:50:

Val Asn Ile Thr Val Lys Gln His Thr Val Thr Thr Thr Thr Lys Gly
1               5                   10                  15
Glu Asn Phe Thr Glu Gly Cys
            20

(2) INFORMATION FOR SEQ ID NO:51:

(i) SEQUENCE CHARACTERISTICS:
        (A) LENGTH: 29 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:51:

Lys His Met Ala Gly Ala Ala Ala Ala Gly Ala Val Val Gly Gly Leu
1               5                   10                  15

Gly Gly Tyr Met Leu Gly Ser Ala Met Ser Arg Gly Cys
            20                  25

(2) INFORMATION FOR SEQ ID NO:52:

(i) SEQUENCE CHARACTERISTICS:
    (A) LENGTH: 33 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /label=X
        / note= "X may be absent or present independently
        of Y and denotes one or amino acid(s)"

(ix) FEATURE:
    (A) NAME/KEY: Modified-site
    (B) LOCATION: 2
    (D) OTHER INFORMATION: /label=X
        / note= "X = either Met, Leu or Phe"

(ix) FEATURE:
    (A) NAME/KEY: Modified-site
    (B) LOCATION: 5
    (D) OTHER INFORMATION: /label=X
        / note= "X = Met or Val"

(ix) FEATURE:
    (A) NAME/KEY: Modified-site
    (B) LOCATION: 11
    (D) OTHER INFORMATION: /label=X
        / note= "X = Ala or absent"

(ix) FEATURE:
    (A) NAME/KEY: Modified-site
    (B) LOCATION: 31
    (D) OTHER INFORMATION: /label=X
        / note= "X = either Leu, Ile or Met"

(ix) FEATURE:
    (A) NAME/KEY: Modified-site
    (B) LOCATION: 32
    (D) OTHER INFORMATION: /label=X
        / note= "X = Leu, Ile or Met"

(ix) FEATURE:
    (A) NAME/KEY: Modified-site
    (B) LOCATION: 33
    (D) OTHER INFORMATION: /label=Y
        / note= "Y may be absent or present independently
        of X and denotes one or more amino acid(s)"

(xi) SEQUENCE DESCRIPTION: SEQ ID NO:52:

Xaa Xaa Lys His Xaa Ala Gly Ala Ala Ala Xaa Gly Ala Val Val Gly
1               5                   10                  15

Gly Leu Gly Gly Tyr Met Leu Gly Ser Ala Met Ser Arg Pro Xaa Xaa
            20                  25                  30

Xaa (2) INFORMATION FOR SEQ ID NO:53:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=X
            / note= "X may be absent or present independently
            of Y and denotes one or more amino acid(s)"

(ix) FEATURE:
        (A) NAME/KEY: Modified-site
        (B) LOCATION: 8
        (D) OTHER INFORMATION: /label=X
            / note= "X = either Leu, Ile, or Met"

(ix) FEATURE:
        (A) NAME/KEY: Modified-site
        (B) LOCATION: 9
        (D) OTHER INFORMATION: /label=X
            / note= "X = either Leu, Ile or Met"

(ix) FEATURE:
        (A) NAME/KEY: Modified-site
        (B) LOCATION: 13
        (D) OTHER INFORMATION: /label=X
            / note= "X = Asn or Ser"

(ix) FEATURE:
        (A) NAME/KEY: Modified-site
        (B) LOCATION: 15
        (D) OTHER INFORMATION: /label=X
            / note= "X = Tyr or Trp"

(ix) FEATURE:
        (A) NAME/KEY: Modified-site
        (B) LOCATION: 25
        (D) OTHER INFORMATION: /label=X
            / note= "X = either His, Tyr or Asn"

(ix) FEATURE:
        (A) NAME/KEY: Modified-site
        (B) LOCATION: 31
        (D) OTHER INFORMATION: /label=Y
            / note= "Y may be absent or present independently
            of X and denotes one or more amino acid(s)"

(xi) SEQUENCE DESCRIPTION: SEQ ID NO:53:

```
Xaa  Ser  Ala  Met  Ser  Arg  Pro  Xaa  Xaa  His  Phe  Gly  Xaa  Asp  Xaa  Glu
1                   5                        10                            15

Asp  Arg  Tyr  Tyr  Arg  Glu  Asn  Met  Xaa  Arg  Tyr  Pro  Asn  Gln  Xaa
               20                        25                       30
```

(2) INFORMATION FOR SEQ ID NO:54:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=X
            / note= "X may be absent or present independently
            of Y and denotes one or more amino acid(s)"

(ix) FEATURE:
    (A) NAME/KEY: Modified-site
    (B) LOCATION: 4
    (D) OTHER INFORMATION: /label=X
        / note= "X = either His, Tyr or Asn"

(ix) FEATURE:
    (A) NAME/KEY: Modified-site
    (B) LOCATION: 15
    (D) OTHER INFORMATION: /label=X
        / note= "X = Val or Met"

(ix) FEATURE:
    (A) NAME/KEY: Modified-site
    (B) LOCATION: 17
    (D) OTHER INFORMATION: /label=X
        / note= "X = either Gln, Glu or Arg"

(ix) FEATURE:
    (A) NAME/KEY: Modified-site
    (B) LOCATION: 19
    (D) OTHER INFORMATION: /label=X
        / note= "X = Ser or Asn"

(ix) FEATURE:
    (A) NAME/KEY: Modified-site
    (B) LOCATION: 31
    (D) OTHER INFORMATION: /label=Y
        / note= "Y may be absent or present independently
        of X and denotes one or more amino acid(s)"

(xi) SEQUENCE DESCRIPTION: SEQ ID NO:54:

Xaa Asn Met Xaa Arg Tyr Pro Asn Gln Val Tyr Tyr Arg Pro Xaa Asp
1                    5                        10                         15

Xaa Tyr Xaa Asn Gln Asn Asn Phe Val His Asp Cys Val Asn Xaa
              20                        25                        30

(2) INFORMATION FOR SEQ ID NO:55:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=X
            / note= "X may be absent or present independently
            of Y and denotes one or more amino acid(s)"

(ix) FEATURE:
        (A) NAME/KEY: Modified-site
        (B) LOCATION: 4
        (D) OTHER INFORMATION: /label=X
            / note= "X = Asp or Gln"

(ix) FEATURE:
        (A) NAME/KEY: Modified-site
        (B) LOCATION: 5
        (D) OTHER INFORMATION: /label=X
            / note= "X = Gly or absent"

(ix) FEATURE:
        (A) NAME/KEY: Modified-site
        (B) LOCATION: 7
        (D) OTHER INFORMATION: /label=X
            / note= "X = Gly or Arg"

(ix) FEATURE:
        (A) NAME/KEY: Modified-site
        (B) LOCATION: 8
        (D) OTHER INFORMATION: /label=X
            / note= "X = Ala or Ser"

( i x ) FEATURE:
   ( A ) NAME/KEY: Modified-site
   ( B ) LOCATION: 10
   ( D ) OTHER INFORMATION: /label=X
         / note= "X = Ser or absent"

( i x ) FEATURE:
   ( A ) NAME/KEY: Modified-site
   ( B ) LOCATION: 11
   ( D ) OTHER INFORMATION: /label=X
         / note= "X = Ala, Thr, Met or Val"

( i x ) FEATURE:
   ( A ) NAME/KEY: Modified-site
   ( B ) LOCATION: 12
   ( D ) OTHER INFORMATION: /label=X
         / note= "X = Val or Ile"

( i x ) FEATURE:
   ( A ) NAME/KEY: Modified-site
   ( B ) LOCATION: 30
   ( D ) OTHER INFORMATION: /label=X
         / note= "X= Ile or Met"

( i x ) FEATURE:
   ( A ) NAME/KEY: Modified-site
   ( B ) LOCATION: 33
   ( D ) OTHER INFORMATION: /label=Y
         / note= "Y may be absent or present independently
         of X and denotes one or more amino acid(s)"

( x i ) SEQUENCE DESCRIPTION: SEQ ID NO:55:

Xaa Tyr Tyr Xaa Xaa Arg Xaa Xaa Ser Xaa Xaa Xaa Leu Phe Ser Ser
1               5                   10                  15

Pro Pro Val Ile Leu Leu Ile Ser Phe Leu Ile Phe Leu Xaa Val Gly
            20                  25                  30

Xaa ( 2 ) INFORMATION FOR SEQ ID NO:56:

( i ) SEQUENCE CHARACTERISTICS:
      ( A ) LENGTH: 33 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /label=X
            / note= "X may be absent or present independently
            of Y and denotes one or more amino acid(s)"

( i x ) FEATURE:
      ( A ) NAME/KEY: Modified-site
      ( B ) LOCATION: 5
      ( D ) OTHER INFORMATION: /label=X
            / note= "X = Gly or absent"

( i x ) FEATURE:
      ( A ) NAME/KEY: Modified-site
      ( B ) LOCATION: 30
      ( D ) OTHER INFORMATION: /label=X
            / note= "X = Gly or absent"

( i x ) FEATURE:
      ( A ) NAME/KEY: Modified-site
      ( B ) LOCATION: 31
      ( D ) OTHER INFORMATION: /label=X
            / note= "X = Gly or Thr"

( i x ) FEATURE:
      ( A ) NAME/KEY: Modified-site (B) LOCATION: 33
(D) OTHER INFORMATION: /label=Y
/ note= "Y may be absent or present independently
of X and denotes one or more amino acid(s)"

(xi) SEQUENCE DESCRIPTION: SEQ ID NO:56:

Xaa Pro Gly Gly Xaa Trp Asn Thr Gly Gly Ser Arg Tyr Pro Gly Gln
1               5                   10                  15

Gly Ser Pro Gly Gly Asn Arg Tyr Pro Pro Gln Gly Gly Xaa Xaa Trp
            20                  25                  30

Xaa (2) INFORMATION FOR SEQ ID NO:57:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=X
/ note= "X may be absent or present independently
of Y and denotes one or more amino acid(s)"

(ix) FEATURE:
(A) NAME/KEY: Modified-site
(B) LOCATION: 4
(D) OTHER INFORMATION: /label=X
/ note= "X = Gly or absent"

(ix) FEATURE:
(A) NAME/KEY: Modified-site
(B) LOCATION: 5
(D) OTHER INFORMATION: /label=X
/ note= "X = Gly or Thr"

(ix) FEATURE:
(A) NAME/KEY: Modified-site
(B) LOCATION: 14
(D) OTHER INFORMATION: /label=X
/ note= "X = Gly or absent"

(ix) FEATURE:
(A) NAME/KEY: Modified-site
(B) LOCATION: 20
(D) OTHER INFORMATION: /label=Y
/ note= "Y may be absent or present independently
of X and denotes on or more amino acid(s)"

(xi) SEQUENCE DESCRIPTION: SEQ ID NO:57:

Xaa Gly Gly Xaa Xaa Trp Gly Gln Pro His Gly Gly Gly Xaa Trp Gly
1               5                   10                  15

Gln Pro His Xaa
            20

(2) INFORMATION FOR SEQ ID NO:58:

(i) SEQUENCE CHARACTERISTICS:
(A) LENGTH: 31 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1

(D) OTHER INFORMATION: /label=X
/ note= "X may be absent or present independently
of Y and denotes one or more amino acid(s)"

(ix) FEATURE:
(A) NAME/KEY: Modified-site
(B) LOCATION: 10
(D) OTHER INFORMATION: /label=X
/ note= "X = Gly or absent"

(ix) FEATURE:
(A) NAME/KEY: Modified-site
(B) LOCATION: 11
(D) OTHER INFORMATION: /label=X
/ note= "X = Thr or Ser"

(ix) FEATURE:
(A) NAME/KEY: Modified-site
(B) LOCATION: 13
(D) OTHER INFORMATION: /label=X
/ note= "X = either Gly, Ser or Asn"

(ix) FEATURE:
(A) NAME/KEY: Modified-site
(B) LOCATION: 19
(D) OTHER INFORMATION: /label=X
/ note= "X = Asn or Ser"

(ix) FEATURE:
(A) NAME/KEY: Modified-site
(B) LOCATION: 24
(D) OTHER INFORMATION: /label=X
/ note= "X = Asn or Ser"

(ix) FEATURE:
(A) NAME/KEY: Modified-site
(B) LOCATION: 25
(D) OTHER INFORMATION: /label=X
/ note= "X = either Met, Leu or Phe"

(ix) FEATURE:
(A) NAME/KEY: Modified-site
(B) LOCATION: 28
(D) OTHER INFORMATION: /label=X
/ note= "X = Val or Met"

(ix) FEATURE:
(A) NAME/KEY: Modified-site
(B) LOCATION: 31
(D) OTHER INFORMATION: /label=Y
/ note= "Y may be absent or present independently
of X and denotes one or more amino acid(s)"

(xi) SEQUENCE DESCRIPTION: SEQ ID NO:58:

Xaa Gly Gly Gly Trp Gly Gln Gly Gly Xaa Xaa His Xaa Gln Trp Asn
1               5                   10                  15

Lys Pro Xaa Lys Pro Lys Thr Xaa Xaa Lys His Xaa Ala Gly Xaa
            20                  25                  30

(2) INFORMATION FOR SEQ ID NO:59:

(i) SEQUENCE CHARACTERISTICS:
(A) LENGTH: 18 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=X
/ note= "X may be absent or present independently
of Y and denotes one or more amino acid(s)"

(ix) FEATURE:

( A ) NAME/KEY: Modified-site
( B ) LOCATION: 2
( D ) OTHER INFORMATION: /label=X
/ note= "X = Ala or Thr"

( i x ) FEATURE:
( A ) NAME/KEY: Modified-site
( B ) LOCATION: 3
( D ) OTHER INFORMATION: /label=X
/ note= "X = either Ser, Pro or Thr"

( i x ) FEATURE:
( A ) NAME/KEY: Modified-site
( B ) LOCATION: 5
( D ) OTHER INFORMATION: /label=X
/ note= "X = Trp or Arg"

( i x ) FEATURE:
( A ) NAME/KEY: Modified-site
( B ) LOCATION: 9
( D ) OTHER INFORMATION: /label=X
/ note= "X = either, Ala, Ser, Pro, and Thr"

( i x ) FEATURE:
( A ) NAME/KEY: Modified-site
( B ) LOCATION: 10
( D ) OTHER INFORMATION: /label=X
/ note= "X = Ala or Thr"

( i x ) FEATURE:
( A ) NAME/KEY: Modified-site
( B ) LOCATION: 11
( D ) OTHER INFORMATION: /label=X
/ note= "X = either Ser, Pro or Thr"

( i x ) FEATURE:
( A ) NAME/KEY: Modified-site
( B ) LOCATION: 13
( D ) OTHER INFORMATION: /label=X
/ note= "X = Trp or Arg"

( i x ) FEATURE:
( A ) NAME/KEY: Modified-site
( B ) LOCATION: 17
( D ) OTHER INFORMATION: /label=X
/ note= "X = either Ala, Ser, Pro, or Thr"

( i x ) FEATURE:
( A ) NAME/KEY: Modified-site
( B ) LOCATION: 18
( D ) OTHER INFORMATION: /label=Y
/ note= "Y may be absent or present independently
of X and denotes one or more amino acid(s)"

( x i ) SEQUENCE DESCRIPTION: SEQ ID NO:59:

Xaa Xaa Xaa Trp Xaa Trp Leu Gly Xaa Xaa Xaa Trp Xaa Trp Leu Gly
1               5                       10                      15

Xaa Xaa ( 2 ) INFORMATION FOR SEQ ID NO:60:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /label=X
/ note= "X may be absent or present independently
of Y and denotes one or more amino acid(s)"

( i x ) FEATURE:

( A ) NAME/KEY: Modified-site
( B ) LOCATION: 2
( D ) OTHER INFORMATION: /label=X
/ note= "X = Ser or Asn"

( i x ) FEATURE:
( A ) NAME/KEY: Modified-site
( B ) LOCATION: 3
( D ) OTHER INFORMATION: /label=X
/ note= "X = either Pro, Leu or His"

( i x ) FEATURE:
( A ) NAME/KEY: Modified-site
( B ) LOCATION: 5
( D ) OTHER INFORMATION: /label=X
/ note= "X = Val or Glu"

( i x ) FEATURE:
( A ) NAME/KEY: Modified-site
( B ) LOCATION: 9
( D ) OTHER INFORMATION: /label=X
/ note= "X = either Val, Ala, Asp or Gly"

( i x ) FEATURE:
( A ) NAME/KEY: Modified-site
( B ) LOCATION: 10
( D ) OTHER INFORMATION: /label=X
/ note= "X = Ser or Asn"

( i x ) FEATURE:
( A ) NAME/KEY: Modified-site
( B ) LOCATION: 11
( D ) OTHER INFORMATION: /label=X
/ note= "X = either Pro, Leu or His"

( i x ) FEATURE:
( A ) NAME/KEY: Modified-site
( B ) LOCATION: 13
( D ) OTHER INFORMATION: /label=X
/ note= "X = Val or Glu"

( i x ) FEATURE:
( A ) NAME/KEY: Modified-site
( B ) LOCATION: 17
( D ) OTHER INFORMATION: /label=X
/ note= "X = either Val, Ala, Asp or Gly"

( i x ) FEATURE:
( A ) NAME/KEY: Modified-site
( B ) LOCATION: 18
( D ) OTHER INFORMATION: /label=Y
/ note= "Y may be absent or present independently
of X and denotes one or more amino acid(s)"

( x i ) SEQUENCE DESCRIPTION: SEQ ID NO:60:

Xaa Xaa Xaa Met Xaa Val Ala Gly Xaa Xaa Xaa Met Xaa Val Ala Gly
1               5                       10                      15

Xaa Xaa ( 2 ) INFORMATION FOR SEQ ID NO:61:

( i ) SEQUENCE CHARACTERISTICS:
( A ) LENGTH: 33 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /label=X
/ note= "X may be absent or present independently
of Y and denotes one or more amino acid(s)"

( i x ) FEATURE:

(A) NAME/KEY: Modified-site
(B) LOCATION: 12
(D) OTHER INFORMATION: /label=X
  / note= "X = Ile or Val"

(ix) FEATURE:
(A) NAME/KEY: Modified-site
(B) LOCATION: 14
(D) OTHER INFORMATION: /label=X
  / note= "X = Gln or Glu"

(ix) FEATURE:
(A) NAME/KEY: Modified-site
(B) LOCATION: 18
(D) OTHER INFORMATION: /label=X
  / note= "X = Val or Thr"

(ix) FEATURE:
(A) NAME/KEY: Modified-site
(B) LOCATION: 31
(D) OTHER INFORMATION: /label=X
  / note= "X = Val or Ile"

(ix) FEATURE:
(A) NAME/KEY: Modified-site
(B) LOCATION: 33
(D) OTHER INFORMATION: /label=Y
  / note= "Y may be absent or present independently
  of X and denotes one or more amino acid(s)"

(xi) SEQUENCE DESCRIPTION: SEQ ID NO:61:

| Xaa | Asn | Phe | Val | His | Asp | Cys | Val | Asn | Ile | Thr | Xaa | Lys | Xaa | His | Thr |
|---|---|---|---|---|---|---|---|---|---|---|---|---|---|---|---|
| 1 | | | | 5 | | | | | 10 | | | | | 15 | |

| Val | Xaa | Thr | Thr | Thr | Lys | Gly | Glu | Asn | Phe | Thr | Glu | Thr | Asp | Xaa | Lys |
|---|---|---|---|---|---|---|---|---|---|---|---|---|---|---|---|
| | | | 20 | | | | | 25 | | | | | 30 | | |

Xaa (2) INFORMATION FOR SEQ ID NO:62:

(i) SEQUENCE CHARACTERISTICS:
(A) LENGTH: 24 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=X
  / note= "X may be absent or present independently
  of Y and denotes one or more amino acid(s)"

(ix) FEATURE:
(A) NAME/KEY: Modified-site
(B) LOCATION: 4
(D) OTHER INFORMATION: /label=X
  / note= "X = either Ile, Thr or Val"

(ix) FEATURE:
(A) NAME/KEY: Modified-site
(B) LOCATION: 8
(D) OTHER INFORMATION: /label=X
  / note= "X = Gln or Glu"

(ix) FEATURE:
(A) NAME/KEY: Modified-site
(B) LOCATION: 9
(D) OTHER INFORMATION: /label=X
  / note= "X = Arg or Lys"

(ix) FEATURE:
(A) NAME/KEY: Modified-site
(B) LOCATION: 16
(D) OTHER INFORMATION: /label=X / note= "X = Asp or Gln"

( i x ) FEATURE:
    ( A ) NAME/KEY: Modified-site
    ( B ) LOCATION: 17
    ( D ) OTHER INFORMATION: /label=X
        / note= "X = Gly or absent"

( i x ) FEATURE:
    ( A ) NAME/KEY: Modified-site
    ( B ) LOCATION: 19
    ( D ) OTHER INFORMATION: /label=X
        / note= "X = Gly or Arg"

( i x ) FEATURE:
    ( A ) NAME/KEY: Modified-site
    ( B ) LOCATION: 20
    ( D ) OTHER INFORMATION: /label=X
        / note= "X = Ala or Ser"

( i x ) FEATURE:
    ( A ) NAME/KEY: Modified-site
    ( B ) LOCATION: 22
    ( D ) OTHER INFORMATION: /label=X
        / note= "X = Ser or absent"

( i x ) FEATURE:
    ( A ) NAME/KEY: Modified-site
    ( B ) LOCATION: 23
    ( D ) OTHER INFORMATION: /label=X
        / note= "X = either Ala, Thr, Met or Val"

( i x ) FEATURE:
    ( A ) NAME/KEY: Modified-site
    ( B ) LOCATION: 24
    ( D ) OTHER INFORMATION: /label=Y
        / note= "Y may be absent or present independently
        of X and denotes one or more amino acid(s)"

( x i ) SEQUENCE DESCRIPTION: SEQ ID NO:62:

Xaa Met Cys Xaa Thr Gln Tyr Xaa Xaa Glu Ser Gln Ala Tyr Tyr Xaa
1               5                   10                  15

Xaa Arg Xaa Xaa Ser Xaa Xaa Xaa
            20

( 2 ) INFORMATION FOR SEQ ID NO:63:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=X
            / note= "X may be absent or present independently of Y and
            denotes one or more amino acid(s)"

( i x ) FEATURE:
        ( A ) NAME/KEY: Modified-site
        ( B ) LOCATION: 3
        ( D ) OTHER INFORMATION: /label=X
            / note= "X = Met or Val"

( i x ) FEATURE:
        ( A ) NAME/KEY: Modified-site
        ( B ) LOCATION: 9
        ( D ) OTHER INFORMATION: /label=X
            / note= "X = Ala or absent"

( i x ) FEATURE:
        ( A ) NAME/KEY: Modified-site
        ( B ) LOCATION: 18

(D) OTHER INFORMATION: /label=Y
/ note= "Y may be absent or present independently of X and denotes one or more amino acid(s)"

(xi) SEQUENCE DESCRIPTION: SEQ ID NO:63:

Xaa His Xaa Ala Gly Ala Ala Ala Xaa Gly Ala Val Val Gly Gly Leu
1               5                       10                      15

Gly Xaa (2) INFORMATION FOR SEQ ID NO:64:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=X
/ note= "X may be absent or present independently of Y and denotes one or more amino acid(s)"

(ix) FEATURE:
(A) NAME/KEY: Modified-site
(B) LOCATION: 17
(D) OTHER INFORMATION: /label=X
/ note= "X = either Leu, Ile, or Met"

(ix) FEATURE:
(A) NAME/KEY: Modified-site
(B) LOCATION: 18
(D) OTHER INFORMATION: /label=X
/ note= "X = either Leu, Ile, or Met"

(ix) FEATURE:
(A) NAME/KEY: Modified-site
(B) LOCATION: 19
(D) OTHER INFORMATION: /label=Y
/ note= "Y may be absent or present independently of X and denotes one or more amino acid(s)"

(xi) SEQUENCE DESCRIPTION: SEQ ID NO:64:

Xaa Gly Gly Leu Gly Gly Tyr Met Leu Gly Ser Ala Met Ser Arg Pro
1               5                       10                      15

Xaa Xaa Xaa (2) INFORMATION FOR SEQ ID NO:65:

(i) SEQUENCE CHARACTERISTICS:
(A) LENGTH: 25 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=X
/ note= "X may be absent or present independently of Y and denotes one or more amino acid(s)"

(ix) FEATURE:
(A) NAME/KEY: Modified-site
(B) LOCATION: 8
(D) OTHER INFORMATION: /label=X
/ note= "X = either Leu, Ile or Met"

(ix) FEATURE:

( A ) NAME/KEY: Modified-site
                    ( B ) LOCATION: 9
                    ( D ) OTHER INFORMATION: /label=X
                           / note= "X = either Leu, Ile or Met"

( i x ) FEATURE:
                    ( A ) NAME/KEY: Modified-site
                    ( B ) LOCATION: 13
                    ( D ) OTHER INFORMATION: /label=X
                           / note= "X = Asn or Ser"

( i x ) FEATURE:
                    ( A ) NAME/KEY: Modified-site
                    ( B ) LOCATION: 15
                    ( D ) OTHER INFORMATION: /label=X
                           / note= "X = Tyr or Trp"

( i x ) FEATURE:
                    ( A ) NAME/KEY: Modified-site
                    ( B ) LOCATION: 25
                    ( D ) OTHER INFORMATION: /label=
                           / note= "Y may be absent or present independently of X and
                           denotes one or more amnio acid(s)"

( x i ) SEQUENCE DESCRIPTION: SEQ ID NO:65:

Xaa  Ser  Ala  Met  Ser  Arg  Pro  Xaa  Xaa  His  Phe  Gly  Xaa  Asp  Xaa  Glu
    1                   5                        10                       15

Asp  Arg  Tyr  Tyr  Arg  Glu  Asn  Met  Xaa
                        20                        25

( 2 ) INFORMATION FOR SEQ ID NO:66:

( i ) SEQUENCE CHARACTERISTICS:
                  ( A ) LENGTH: 28 amino acids
                  ( B ) TYPE: amino acid
                  ( C ) STRANDEDNESS: single
                  ( D ) TOPOLOGY: linear ( i i ) MOLECULE TYPE: peptide ( i x ) FEATURE:
                  ( A ) NAME/KEY: Modified-site
                  ( B ) LOCATION: 1
                  ( D ) OTHER INFORMATION: /label=X
                         / note= "X may be absent or present independently of Y and
                         denotes one or more amino acid(s)"

( i x ) FEATURE:
                  ( A ) NAME/KEY: Modified-site
                  ( B ) LOCATION: 12
                  ( D ) OTHER INFORMATION: /label=X
                         / note= "X = Val or Met"

( i x ) FEATURE:
                  ( A ) NAME/KEY: Modified-site
                  ( B ) LOCATION: 14
                  ( D ) OTHER INFORMATION: /label=X
                         / note= "X = either Gln, Glu or Arg"

( i x ) FEATURE:
                  ( A ) NAME/KEY: Modified-site
                  ( B ) LOCATION: 16
                  ( D ) OTHER INFORMATION: /label=X
                         / note= "X = Ser or Asn"

( i x ) FEATURE:
                  ( A ) NAME/KEY: Modified-site
                  ( B ) LOCATION: 28
                  ( D ) OTHER INFORMATION: /label=Y
                         / note= "Y may be absent or present independently of X and
                         denotes one or more amino acid(s)"

( x i ) SEQUENCE DESCRIPTION: SEQ ID NO:66:

Xaa  Arg  Tyr  Pro  Asn  Gln  Val  Tyr  Tyr  Arg  Pro  Xaa  Asp  Xaa  Tyr  Xaa
    1                   5                        10                       15

-continued

Asn Gln Asn Asn Phe Val His Asp Cys Val Asn Xaa
20 25

( 2 ) INFORMATION FOR SEQ ID NO:67:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /label=X
/ note= "X may be absent or present independently of Y and denotes one or more amino acid(s)"

( i x ) FEATURE:
( A ) NAME/KEY: Modified-site
( B ) LOCATION: 2
( D ) OTHER INFORMATION: /label=X
/ note= "X = Gly or Arg"

( i x ) FEATURE:
( A ) NAME/KEY: Modified-site
( B ) LOCATION: 3
( D ) OTHER INFORMATION: /label=X
/ note= "X = Ala or Ser"

( i x ) FEATURE:
( A ) NAME/KEY: Modified-site
( B ) LOCATION: 5
( D ) OTHER INFORMATION: /label=X
/ note= "X = Ser or absent"

( i x ) FEATURE:
( A ) NAME/KEY: Modified-site
( B ) LOCATION: 6
( D ) OTHER INFORMATION: /label=X
/ note= "X = either Ala, Thr, Met or Val"

( i x ) FEATURE:
( A ) NAME/KEY: Modified-site
( B ) LOCATION: 7
( D ) OTHER INFORMATION: /label=X
/ note= "X = Val or Ile"

( i x ) FEATURE:
( A ) NAME/KEY: Modified-site
( B ) LOCATION: 20
( D ) OTHER INFORMATION: /label=Y
/ note= "Y may be absent or present independently of X and denotes one or more amino acid(s)"

( x i ) SEQUENCE DESCRIPTION: SEQ ID NO:67:

Xaa Xaa Xaa Ser Xaa Xaa Xaa Leu Phe Ser Ser Pro Pro Val Ile Leu
1 5 10 15

Leu Ile Ser Xaa
20

FRAGMENTS OF PRION PROTEINS

This application is a 371 of PCT/GB92/02246, filed Dec. 3, 1992.

The present invention relates to synthetic polypeptides. In particular it relates to synthetic polypeptides which emulate the three-dimensional structures and/or electrostatic surfaces and/or other physical, chemical and structural properties of specific regions of proteins thought to be the involved in the molecular pathology of spongiform encephalopathies. It is of particular interest to the design of immunodiagnostics, vaccines and other medical, veterinary or scientific agents in relation to human, bovine and ovine spongiform encephalopathies.

Spongiform encephalopathies are a group of degenerative neurological diseases. Examples have been found in a number of species including sheep (where it is known as scrapie), cows (BSE) and humans (Creutzfeldt-Jakob disease (CJD) and kuru) (Review article, Taylor, D. M. Veterinary Record 125, 413–415 (1989)). Similar conditions have also been found in the wild mink population and in captive kudus (a kind of antelope) and tigers. It has been variously reported that BSE can be transmitted under laboratory conditions to mice and pigs. This crossing of species barriers by the infective agent has led to increased concern that transfer to humans could occur.

These diseases are characterised by a slow incubation time of four to five years after which the clinical symptoms of progressive degeneration of mental state, including aggressiveness and lack of coordination, appear. Post mortems reveal a characteristic pattern of vacuolation in brain tissue due to the destruction of neural cells, and the deposition of unusual protein fibres.

Although the form of the disease found in sheep (scrapie) has been known for many years, spongiform encephalopathies have come to prominence within the last decade following the appearance of BSE in cattle farms. The incidence of BSE in the United Kingdom has increased markedly during this period and public concern over the possible transmission of the disease to humans has led to a collapse in the beef market. Thus for both veterinary and economic reasons, there is an urgent need for diagnostic agents to detect infection and for vaccines to prevent infection.

It is believed that the causative agent of scrapie and its counterparts in other animals is a so-called "prion", that is an infective particle comprising protein only and no nucleic acid, the presence of the latter being required in the case of a conventional virus. In scrapie, one particular protein (termed prion protein, $PrP^{SC}$) has been found to co-purify with infectivity and can produce a scrapie-like condition in brain cell cultures from other animals, such as hamsters, under laboratory conditions. $PrP^{SC}$ is the only known component of the characteristic protein fibres deposited in the brain tissue of scrapie-infected sheep. The term "$PrP^{SC}$" as used herein should be taken to refer not only to the specific Prion protein identified in sheep but also to those homologous proteins found in many other species which appear to undergo a structural modification as described hereinafter. The term "$PrP^C$" shall be used in respect of the normal cellular counterpart to $PrP^{SC}$.

The major problem in the search for a specific diagnostic agent or synthetic vaccine against the scrapie agent $PrP^{SC}$ is that it is almost identical to the natural form of the protein $PrP^C$. The natural function of this protein is not yet understood but the remarkably strong conservation of primary structure between homologous proteins from different species suggests that it has an essential structural or functional role within the organism.

In spite of the almost identical form of these prions to the natural proteins, we have deduced synthetic peptide structures comprising at least one antigenic property, such as an epitopic site and these synthetic peptides may be used to produce diagnostic agents and vaccines.

The responses of the B and T cells of the immune system are not specified by a global recognition of a whole protein but rather by recognition of a small region of the protein surface known as epitopic site. Such sites may be formed by a continuous section of peptide chain or may be discontinuous, where separated sections of peptide chain are brought together at the protein surface due to folding of the chain. One aim in producing a synthetic peptide vaccine is to mimic the structure of a particular epitope and thereby cause a primary immune response leading to the production of memory B cells which will secrete antibodies on subsequent exposure to the parent protein so producing a greatly enhanced response to secondary infection. A similar mechanism via priming of the cytotoxic T cells to respond more vigorously to a particular antigen will also occur.

However, problems exist with the application of traditional methods of vaccine production to this disease as it is believed that the molecular structure of the protein prion rather than nucleic acid sequence passes on infectivity in the prion. The usual method of viral vaccine production involves the inactivation of the virus in some way to destroy infectivity whilst preserving epitopic sites. Such techniques as heat treatment or serial passaging of the virus through a culture are used, but these approaches would not lead to a loss of infectivity of a prion unless conditions were such as to cause protein denaturation. If the conditions are severe enough to inactivate the prion protein then denaturation of the protein occurs and any epitopic sites are lost. Thus there is a major problem in trying to obtain antigenic but non-infective prion proteins by conventional routes. It is known, for example, that the scrapie agent in sheep is particularly resistant to chemical or physical inactivation (Hodgson, J. Bio/Technology 8 990 (1990)).

In one aspect our invention provides a synthetic polypeptide having at least one antigenic site of a prion protein. Preferably the prion protein is of a form which only exists in nervous tissue of a mammal suffering from spongiform encephalopathy.

We have found that prion proteins of the type mentioned above comprise six regions of interest, labelled A to F, and two related frame shift peptide sequences, viz:1) a repeating section in region E having undergone a nucleic acid coding sequence frame shift of +1 (FSa) and 2) the repeating section in region E having undergone a nucleic acid coding sequence frame shift of −1 (FSb).

With regard to region A, our invention provides a synthetic peptide sequence according to general formula (I), SEQ ID NO:52 :

(I(Sequence ID NO: 52))
X—($R_1$—Lys—His—$R_2$)—Ala—Gly—Ala—Ala—Ala—$R_3$—Gly—Ala—Val—Val—Gly—Gly—Leu—Gly—Gly—Tyr—Met—Leu—Gly—Ser—Ala—Met—Ser—(Arg—Pro—$R_4$—$R_5$)—Y wherein $R_1$ is an amino acid residue selected from Met, Leu and Phe;

$R_2$ is either Met or Val;

$R_3$ is Ala or is absent;

$R_4$ and $R_5$ are independently an amino acid residue selected from Leu, Ile and Met; one or more residues within brackets maybe present or absent with the proviso that if they are present they are attached to the rest of the peptide in sequence; and X and Y may each independently be absent or independently be one or more additional amino acid residues.

It will be apparent for example that the residues at the N-terminal of the sequence may be present as "$R_2$"- or "His-$R_2$-," or "Lys-His-$R_2$-" or "$R_1$-Lys-His-$R_2$-." Similarly, the preferable residues at the C-terminal may be present as "-Arg", or "-Arg-Pro," or "-Arg-Pro-$R_4$," or "-Arg-Pro-$R_4$-$R_5$."

Preferably, $R_1$, if present, is Met, $R_3$, is Ala and $R_5$, if present, is Ile. Also, if $R_2$ is Met then $R_4$, if present, is Ile. Below are preferred sequences (Seq. I.D. No: 1 and Seq. I.D. No: 2) of formula I (SEQ ID NO:52) relating to bovine and ovine and to human prion proteins respectively:

Seq. I.D. No: 1
X — (Met — Lys — His — Val) — Ala — Gly — Ala — Ala — Ala —
Ala — Gly — Ala — Val — Val — Gly — Gly — Leu — Gly — Gly —
Tyr — Met — Leu — Gly — Ser — Ala — Met — Ser — (Arg — Pro —
Leu — Ile) — Y;

and

Seq. I.D. No: 2
X — (Met — Lys — His — Met) — Ala — Gly — Ala — Ala — Ala —
Ala — Gly — Ala — Val — Val — Gly — Gly — Leu — Gly — Gly —
Tyr — Met — Leu — Gly — Ser — Ala — Met — Ser — (Arg — Pro —
Ile — Ile) — Y.

A particularly preferred sequence according to formula I (SEQ ID NO: 52) is Seq. I.D. No:5

Lys — His — Met — Ala — Gly — Ala — Ala — Ala — Ala — Gly —
Ala — Val — Val — Gly — Gly — Leu — Gly — Gly — Tyr — Met —
Leu — Gly — Ser — Ala — Met — Ser — Arg — Gly — Cys.

Naturally, our invention encompasses significant sub-fragments of the sequence according to formula I (SEQ ID NO:52) above and preferred sub-fragments are:

i) X — (His — $R_2$ — Ala — Gly) — Ala — Ala — Ala — $R_3$ — Gly —
Ala — Val — Val — (Gly — Gly — Leu — Gly) — Y and;

ii) X — (Gly — Gly — Leu — Gly) — Gly — Tyr — Met — Leu —
Gly — Ser — Ala — Met — Ser — (Arg — Pro — $R_4$ — $R_5$) — Y wherein $R_2$, $R_3$, $R_4$, $R_5$, X and Y are as defined for formula I (SEQ ID NO:52) and one or more residues in brackets may be absent or present as in formula I (SEQ ID NO:52).

It will be clear from the foregoing that preferred sub-fragments relating to both bovines and ovines are Seq. I.D. No: 3
i) X — (His — Val — Ala — Gly) — Ala — Ala — Ala — Ala — Gly —
Ala — Val — Val — Gly — (Gly — Leu — Gly — Gly) — Y and Seq. I.D. No: 4
ii) X — (Gly — Gly — Leu — Gly) — Gly — Tyr — Met — Leu —
Gly — Ser — Ala — Met — Ser — (Arg — Pro — Leu — Ile) — Y.

Similarly, preferred sub-fragments for humans are:

Seq. I.D. No: 5
i) X — (His — Met — Ala — Gly) — Ala — Ala — Ala — Ala — Gly —
Ala — Val — Val — Gly — (Gly — Leu — Gly — Gly) — Y and Seq. I.D. No: 6
ii) X — (Gly — Gly — Leu — Gly) — Gly — Tyr — Met — Leu —
Gly — Ser — Ala — Met — Ser — (Arg — Pro — Ile — Ile) — Y.

With regard to region B, our invention provides a synthetic peptide sequence according to general formula II, (SEQ ID NO:53):

(II(Sequence ID NO: 53))
X — (Ser — Ala — Met — Ser) — Arg — Pro — $R_4$ — $R_5$ — His —
Phe — Gly — $R_6$ — Asp — $R_7$ — Glu — Asp — Arg — Tyr —
Tyr — Arg — Glu — Asn — Met — $R_8$ — Arg — (Tyr — Pro —
Asn — Gln) — Y wherein $R_4$ and $R_5$ are the same as in formula I (SEQ ID NO:52);

$R_6$ is either Asn or Ser;

$R_7$ is either Tyr or Trp;

$R_8$ is an amino acid residue selected from His, Tyr and Asn;

one or more residues within brackets maybe present or absent with the proviso that if they are present they are attached to the rest of the peptide in sequence; and X and Y may each independently be absent or independently be one or more additional amino acid residues.

Preferably in a sequence according to formula II (SEQ ID NO:53), $R_5$ is Ile, $R_7$ is Tyr and $R_8$ is His or Tyr. Below are preferred sequences of formula II (SEQ ID NO:53) relating to bovine, ovine and human prion proteins respectively:

Seq. I.D. No: 7
X — (Ser — Ala — Met — Ser) — Arg — Pro — Leu — Ile — His —
Phe — Gly — Ser — Asp — Tyr — Glu — Asp — Arg — Tyr — Tyr —
Arg — Glu — Asn — Met — His — Arg —
(Tyr — Pro — Asn — Gln) — Y;

Seq. I.D. No: 8
X — (Ser — Ala — Met — Ser) — Arg — Pro—Leu—Ile—His—Phe—Gly—Asn—Asp—Tyr—Glu—Asp—Arg—Tyr—Tyr—Arg—Glu—Asn—Met—Tyr—Arg—(Tyr—Pro—Asn—Gln)—Y;

and

Seq. I.D. No: 9
X—(Ser—Ala—Met—Ser)—Arg—Pro—Ile—Ile—His—Phe—Gly—Ser—Asp—Tyr—Glu—Asp—Arg—Tyr—Tyr—Arg—Glu—Asn—Met—His—Arg—(Tyr—Pro—Asn—Gln)—Y.

Particularly preferred sequences are selected from

Seq. I.D. No: 42
Ser—Ala—Met—Ser—Arg—Pro—Leu—Ile—His—Phe—Gly—Asn—Asp—Tyr—Glu—Asp—Arg—Tyr—Tyr—Gly—Cys ;

and

Seq. I.D. No: 43
Ser—Ala—Met—Ser—Arg—Pro—Leu—Ile—His—Phe—Gly—Ser—Asp—Tyr—Glu—Asp—Arg—Tyr—Tyr—Gly—Cys.

Again it will be apparent that our invention encompasses significant sub-fragments of the sequence according to Formula II (SEQ ID NO:53) and a preferred general sub-fragment has the sequence:

X—(Ser—Ala—Met—Ser)—Arg—Pro—$R_4$—$R_5$—His—Phe—Gly—$R_6$—Asp—$R_7$—Glu—Asp—Arg—Tyr—Tyr—(Arg—Glu—Asn—Met)—Y wherein $R_4$, to $R_7$, X and Y are as defined in formula II (SEQ ID NO:53) and one or more residues in brackets may be present or absent. Preferably, $R_5$ is Ile and $R_7$ is Tyr. It will be appreciated that preferred sub-fragments relating to bovines, ovines and humans are respectively, Seq. I.D. No: 10
X — (Ser — Ala — Met — Ser) — Arg — Pro — Leu — Ile — His —
Phe — Gly — Ser — Asp — Tyr — Glu — Asp — Arg — Tyr — Tyr —
(Arg — Glu — Asn — Met) — Y;

Seq. I.D. No: 11
X — (Ser — Ala — Met — Ser) — Arg — Pro — Leu — Ile — His —
Phe — Gly — Asn — Asp — Tyr — Glu — Asp — Arg — Tyr — Tyr —
(Arg — Glu — Asn — Met) — Y;

and

Seq. I.D. No: 12
X — (Ser — Ala — Met — Ser) — Arg — Pro — Ile — Ile — His —
Phe — Gly — Ser — Asp — Tyr — Glu — Asp — Arg — Tyr — Tyr —
(Arg — Glu — Asn — Met) — Y.

Our invention provides in respect of region C a synthetic peptide sequence according to general formula III, (SEQ ID NO:54):

(III(SEQ ID NO: 54))
X — (Asn — Met — $R_8$ — Arg) — Tyr — Pro — Asn — Gln — Val —
Tyr — Tyr — Arg — Pro — $R_9$ — Asp — $R_{10}$ — Tyr — $R_{11}$ — Asn —
Gln — Asn — Asn — Phe — Val — His —
(Asp — Cys — Val — Asn) — Y wherein $R_8$ is an amino acid residue selected from His, Tyr and Asn;

$R_9$ is Val or Met;

$R_{10}$ is an amino acid residue selected from Gln, Glu and Arg;

$R_{11}$ is Ser or Asn; one or more residues within brackets maybe present or absent with the proviso that if they are present they are attached to the rest of the peptide in sequence and X and Y may each independently be absent or independently be one or more additional amino acid residues.

Preferably in a sequence according to formula III (SEQ ID NO:54), $R_8$ is His or Tyr and $R_{11}$ is Ser. Below are preferred sequences of formula III (SEQ ID NO:54) relating to bovine, ovine and human prion proteins respectively:

Seq. I.D. No: 13
X — (Asn — Met — His — Arg) — Tyr — Pro — Asn — Gln — Val —
Tyr — Tyr — Arg — Pro — Val — Asp — Gln — Tyr — Ser — Asn —
Gln — Asn — Asn —

-continued

Seq. I.D. No: 20
X—(Tyr—Tyr—Gln—Arg)—Gly—Ser—Ser—Met—Val—
Leu—Phe—Ser—Ser—Pro—Pro—Val—Ile—Leu—Leu—
Ile—Ser—Phe—Leu—Ile—Phe—Leu—Ile—Val—Gly—Y.

Clearly, it will be recognised that the present invention includes with its ambit significant sub-fragments of the sequence according to formula IV and a preferred general sub-fragment has the sequence:

X—(—$R_{14}$—$R_{15}$—Ser—$R_{16}$—$R_{17}$)—$R_{18}$—Leu—Phe—Ser—
Ser—Pro—Pro—Val—Ile—(Leu—Leu—Ile—Ser)—Y

Wherein $R_{14}$, to $R_{18}$, X and Y are as defined in formula IV (SEQ ID NO:55) and one or more residues within brackets may be present or absent as in formula IV (SEQ ID NO:55).

It is preferred that in a sub-fragment as given above, $R_{14}$ is Gly, $R_{16}$ is absent and $R_{17}$ is Val or Met. Below are preferred sub-fragments relating to bovines and ovines and to humans respectively:

Seq. I.D. No: 21
X—(Gly—Ala—Ser—Val—)Ile—Leu—Phe—Ser—Ser—
Pro—Pro—Val—Ile—(Leu—Leu—Ile—Ser)—Y;

and

Seq. I.D. No: 22
X—(Gly—Ser—Ser—Met)—Val—Leu—Phe—Ser—Ser—
Pro—Pro—Val—Ile—(Leu—Leu—Ile—Ser)—Y.

Our invention provides in respect of Region E three synthetic polypeptide sequences according to general formulae Va (SEQ ID NO:56), Vb (SEQ ID NO:57) and Vc (SEQ ID NO:58):

X—(Pro—Gly—Gly—$R_{20}$)—Trp—Asn—Thr—Gly—Gly—
Ser—Arg—Tyr—Pro—Gly—Gln—Gly—Ser—Pro—Gly—
Gly—Asn—Arg—Tyr—Pro—Pro—Gln—Gly—(Gly—$R_{21}$—
$R_{22}$—Trp)—Y    (Va(SEQ ID No: 56);

X—(Gly—Gly—$R_{21}$—$R_{22}$—Trp)—Gly—Gln—Pro—His—
Gly—Gly—Gly—$R_{23}$—Trp (Gly—Gln—Pro—His)—Y (Vb (SEQ ID NO: 57);

and

X—(Gly—Gly—Gly—Trp)—Gly—Gln—Gly—Gly—$R_{24}$—
$R_{25}$—His—$R_{26}$—Gln—Trp—Asn—Lys—Pro—$R_{27}$—Lys—
Pro—Lys—Thr—$R_{28}$—$R_{29}$—Lys (—His—$R_{30}$—Ala—Gly)—
Y (Vc(SEQ ID NO: 58)

Wherein $R_{20}$, $R_{21}$, $R_{23}$ and $R_{24}$ are each independently either Gly or absent,
$R_{22}$ either Gly or Thr;
$R_{25}$ is either Thr or Ser;
$R_{26}$ is an amino acid residue selected from Gly, Ser and Asn;
$R_{27}$ and $R_{28}$ are each independently either Asn or Ser;
$R_{29}$ is an amino acid residue selected from Met, Leu and Phe;
$R_{30}$ is either Val or Met; one or more residues within brackets maybe present or absent with the proviso that if they are present they are attached to the rest of the peptide in sequence; and X and Y may each independently be absent or independently be one or more additional amino acid residues.

With regard to formulae Va to Vc above, it is preferred that $R_{22}$ is Gly, $R_{23}$ is absent, $R_{26}$ is Gly or Ser, $R_{27}$ is Ser, $R_{28}$ is Asn and $R_{29}$ is Met.

Preferred bovine sequences of prion proteins according to formulae Va to Vc are given below:

Seq. I.D. No: 23
X—(Pro—Gly—Gly—Gly)—Trp—Asn—Thr—Gly—Gly—
Ser—Arg—Tyr—Pro—Gly—Gln—Gly—Ser—Pro—Gly—
Gly—Asn—Arg—Tyr—Pro—Pro—Gln—Gly—(Gly—Gly—
Gly—Trp)—Y;

Seq. I.D. No: 24
X—(Gly—Gly—Gly—Trp)—Gly—Gln—Pro—His—Gly—
Gly—Gly—Trp—(Gly—Gln—Pro—His)—Y;

and

Seq. I.D. No: 25
X—(Gly—Gly—Gly—Trp)—Gly—Gln—Gly—Gly—Thr—
His—Gly—Gln—Trp—Asn—Lys—Pro—Ser—Lys—Pro—
Lys—Thr—Asn—Met—Lys (—His—Val—Ala—Gly)—Y.

Preferred sequences of formulae Va to Vc relating to ovine prion proteins are as follows:

Seq. I.D. No: 26
X—(Pro—Gly—Gly—Gly)—Trp—Asn—Thr—Gly—Gly—
Ser—Arg—Tyr—Pro—Gly—Gln—Gly—Ser—Pro—Gly—
Gly—Asn—Arg—Tyr—Pro—Pro—Gln—Gly—(Gly—Gly—
Gly—Trp)—Y;

Seq I.D. No: 27
X—(Gly—Gly—Gly—Trp)—Gly—Gln—Pro—His—Gly—
Gly—Gly—Trp—(Gly—Gln—Pro—His)—Y;

and

Seq. I.D. No: 28
X—(Gly—Gly—Gly—Trp)—Gly—Gln—Gly—Gly—Ser—
His—Ser—Gln—Trp—Asn—Lys—Pro—Ser—Lys—Pro—
Lys—Thr—Asn—Met—Lys (—His—Val—Ala—Gly)—Y.

Preferred sequences of formulae Va to Vc relating to human prion proteins are as follows:

Seq. I.D. No: 29
X—Pro—Gly—Gly—Gly—Trp—Asn—Thr—Gly—Gly—
Ser—Arg—Tyr—Pro—Gly—Gln—Gly—Ser—Pro—Gly—
Gly—Asn—Arg—Tyr—Pro—Pro—Gln—Gly—(Gly—Gly—
Gly—Trp)—Y;

Seq. I.D. No: 30
X—(Gly—Gly—Gly—Trp)—Gly—Gln—Pro—His—Gly—
Gly—Gly—Trp—(Gly—Gln—Pro—His)—Y;

and

Seq. I.D. No: 31
X—(Gly—Gly—Gly—Trp)—Gly—Gln—Gly—Gly—Gly—
Thr—His—Ser—Gln—Trp—Asn—Lys—Pro—Ser—Lys—
Pro—Lys—Thr—Asn—Met—Lys(—His—Met—Ala—Gly)
—Y.

Particularly preferred sequences of formulae Va to Vc consist of:

Seq. I.D. No: 49
Gly—Gly—Trp—Asn—Thr—Gly—Gly—Ser—Arg—Tyr—
Pro—Gly—Gln—Gly—Ser—Pro—Gly—Gly—Asn—Arg—
Tyr—Pro—Pro—Gln—Gly—Gly—Gly—Cys;

Seq. I.D. No: 46
Gly—Gln—Pro—His—Gly—Gly—Gly—Trp—Gly—Gln—
Pro—His—Gly—Gly—Gly—Trp—Gly—Gln—Pro—His—
Gly—Gly—Gly—Trp—Gly—Cys;

and

Seq. I.D. No: 47
Gly—Gln—Gly—Gly—Ser—His—Ser—Gln—Trp—Asn—
Lys—Pro—Ser—Lys—Pro—Lys—Thr—Asn—Met—Lys—
His—Val—Gly—Cys.

We have noted that in the nucleic acid sequence corresponding to region E, it is possible for the repeating sequence of formula Vb (SEQ ID NO:57) to have undergone a frame shift of either +1 or −1. Such frame shifts give rise to altered sequences in region E of the prion protein and our invention provides a synthetic polypeptide having a sequence wherein a repeat in region E has undergone a −1 frame shift as given in formula VI, (SEQ ID NO:59):

X—($R_{31}$—$R_{32}$—Trp—$R_{33}$)—Trp—Leu—Gly—$R_{34}$—$R_{35}$—$R_{36}$—Trp—$R_{37}$(Trp—Leu—Gly—$R_{38}$)—Y (VI (SEQ ID No: 59)).

Wherein $R_{31}$ and $R_{35}$ are each independently either Ala or Thr; $R_{32}$ and $R_{36}$ are each independently an amino acid residue selected from Ser, Pro and Thr; $R_{33}$ and $R_{37}$ are each independently either Trp or Arg; $R_{34}$ and $R_{38}$ are each independently an amino acid residue selected from Ala, Ser, Pro and Thr; one or more residues within brackets maybe present or absent with the proviso that if they are present they are attached to the rest of the peptide in sequence; and X and Y may each independently be absent or independently be one or more, additional amino acid residues.

With regard to −1 frame shifts in respect of region E in bovines, it is preferred that $R_{31}$ is Ala, $R_{32}$, $R_{34}$, $R_{36}$ and $R_{38}$ are each independently either Ser or Pro, $R_{33}$ and $R_{37}$ are Arg and $R_{35}$ is Ala.

It should be noted that preferred sequences for −1 frame shifts in region E of ovines differ in some respects to those given for bovines and in a referred ovine sequence $R_{31}$, $R_{32}$, $R_{33}$, $R_{35}$, $R_{36}$ and $R_{37}$ correspond to the definitions given for formula VI (SEQ ID NO:59) above; and $R_{34}$ and $R_{38}$ are each independently selected from Ser, Pro and Thr.

In a preferred human sequence according to formula VI (SEQ ID NO:59)$R_{31}$, $R_{34}$, $R_{35}$ and $R_{38}$ are each Ala, $R_{32}$ and $R_{36}$ are each independently either Ser or Pro and $R_{33}$ and $R_{37}$ are both Trp.

As mentioned previously, the frame shift may be +1 in the repeat portion of region E and this gives rise to different amino acid sequences. Accordingly, our invention provides a synthetic polypeptide according to formula VII (SEQ ID NO:60) below which relates to a +1 frame shift in the repeat of region E:

X—($R_{39}$—$R_{40}$—Met—$R_{41}$)—Val—Ala—Gly—$R_{42}$—$R_{43}$—$R_{44}$—Met—$R_{45}$—(Val—Ala—Gly—$R_{46}$)—Y (VII (SEQ ID No: 60))

Wherein $R_{39}$ and $R_{43}$ are each independently either Ser or Asn; $R_{40}$ and $R_{44}$ are each independently an amino acid residue selected from Pro, Leu and His, $R_{41}$, and $R_{45}$ are each independently Val or Glu; $R_{42}$ and $R_{46}$ are each independently selected from Val, Ala, Asp and Gly; one or more residues within brackets maybe present or absent with the proviso that if they are present they are attached to the rest of the peptide in sequence; and X and Y may each independently be absent or independently be one or more, additional amino acid residues.

A preferred bovine sequence according to formula VII comprises $R_{39}$ and $R_{43}$ each being Ser, $R_{42}$ and $R_{46}$ each being independently either Val or Ala and $R_{44}$ being either Pro or Leu; with the other R groups being as defined in formula VII (SEQ ID NO:60).

A preferred sequence according to formula VII (SEQ ID NO:60) relating to ovines is the same as given in general formula VII except $R_{42}$ and $R_{46}$ are each independently selected from Val, Ala and Asp.

With regard to a preferred human sequence according to formula VII, $R_{39}$ and $R_{43}$ are Ser, $R_{40}$ and $R_{44}$ are each independently Pro or Leu, $R_{41}$ and $R_{45}$ are Val and $R_{42}$ and $R_{46}$ are each independently either Asp or Gly.

Our invention also provides a synthetic peptide sequence relating to region F and having either the general formula VIIIa (SEQ ID NO:61) or VIIIb (SEQ ID NO:62):

X—(Asn—Phe—Val—His)—Asp—Cys—Val—Asn—Ile—Thr—$R_{47}$—Lys—$R_{48}$—His—Thr—Val—$R_{49}$—Thr—Thr—Thr—Lys—Gly—Glu—Asn—Phe—Thr—Glu—(Thr—Asp—$R_{50}$—Lys)—Y (VIIIa(SEQ ID NO: 61))

X—(Met—Cys—$R_{51}$—Thr)—Gln—Tyr—$R_{52}$—$R_{53}$—Glu—Ser—Gln—Ala—Tyr—Tyr—$R_{54}$—$R_{55}$—Arg—($R_{56}$—$R_{57}$—Ser—$R_{58}$—$R_{59}$)—Y (VIIIb(SEQ ID No: 62))

Wherein $R_{47}$ is either Ile or Val;

$R_{48}$ and $R_{52}$ are each independently either Gln or Glu;

$R_{49}$ is either Val or Thr;

$R_{50}$ is either Val or Ile;

$R_{51}$ is an amino acid residue selected from Ile, Thr and Val;

$R_{52}$ is Gln or Glu;

$R_{53}$ is either Arg or Lys;

$R_{54}$ is either Asp or Gln;

$R_{55}$ is Gly or is absent;

$R_{56}$ is either Gly or Arg;

$R_{57}$ is either Ala or Ser;

$R_{58}$ is Ser or absent;

$R_{59}$ is an amino acid residue selected from Ala, Thr, Met and Val;

one or more residues within brackets maybe present or absent with the proviso that if they are present they are attached to the rest of the peptide in sequence; and X and Y may each independently be absent or independently be one or more, e.g. 3, additional amino acid residues.

It is preferred in formula VIIIa (SEQ ID NO:61) that $R_{49}$ is Thr and in formula VIIIb (SEQ ID NO:62) that $R_{51}$ is Ile, $R_{53}$ is Arg, $R_{54}$ is Gln, $R_{55}$ is absent, $R_{56}$ is Gly, $R_{57}$ is Ala and $R_{58}$ is absent.

Most preferred bovine, ovine and human sequences according to formulae VIIIa (SEQ ID NO:61) and VIIIb (SEQ ID NO:62) are given below in order:

Seq. I.D. No: 32
X—(Asn—Phe—Val—His)—Asp—Cys—Val—Asn—Ile—Thr—Val—Lys—Glu—His—Thr—Val—Thr—Thr—Thr—Thr—Lys—Gly—Glu—Asn—Phe—Thr—Glu—(Thr—Asp—Ile—Lys)—Y
bovine (VIIIa), and Seq. I.D. No: 33
X—(Met—Cys—Ile—Thr)—Gln—Tyr—Gln—Arg—Glu—Ser—Gln—Ala—Tyr—Tyr—Gln—Arg—(Gly—Ala—Ser—Val)—Y
bovine (VIIIb);

Seq. I.D. No: 34
X—(Asn—Phe—Val—His)—Asp—Cys—Val—Asn—Ile—Thr—Val—Lys—Gln—His—Thr—Val—Thr—Thr—Thr—Thr—Lys—Gly—Glu—Asn—Phe—Thr—Glu—(Thr—Asp—Ile—Lys)—Y
ovine (VIIIa), and Seq. I.D. No: 35
X—(Met—Cys—Ile—Thr)—Gln—Tyr—Gln—Arg—Glu—Ser—Gln—Ala—Tyr—Tyr—Gln—Arg—(Gly—Ala—Ser—Val)—Y
ovine (VIIIb);

Seq. I.D. No: 36
X—(Asn—Phe—Val—His)—Asp—Cys—Val—Asn—Ile—Thr—Ile—Lys—Gln—His—Thr—Val—Thr—Thr—Thr—

-continued

Thr—Lys—Gly—Glu—Asn—Phe—Thr—Glu—(Thr—Asp—Val—Lys)—Y
human (VIIIa), and

Seq. I.D. No: 37
X—(Met—Cys—Ile—Thr)—Gln—Tyr—Glu—Arg—Glu—Ser—Gln—Ala—Tyr—Tyr—Gln—Arg—(Gly—Ser—Ser—Met)—Y
human (VIIIb).

Particularly preferred sequences according to formula VIIIa (SEQ ID NO:61) and VIIIb (SEQ ID NO:62) are selected from Seq. I.D. No: 50
Val—Asn—Ile—Thr—Val—Lys—Gln—His—Thr—Val—Thr—Thr—Thr—Thr—Lys—Gly—Glu—Asn—Phe—Thr—Glu—Gly—Cys;

and

Seq. I.D. No: 48
Cys—Ile—Thr—Gln—Tyr—Gln—Arg—Glu—Ser—Gln—Ala—Tyr—Tyr—Gln—Arg.

Synthetic polypeptides according to any one of formulae I (SEQ ID NO:52) to VIIIb (SEQ ID NO:62) above without X and Y being present will of course be useful, for example, in the production of antibodies. However, when X or Y are present they may be any length but preferably less than 20 amino acids, more preferably less than 10, eg. 3 to 6. It will of course be appreciated that a sequence according to any one of formulae I (SEQ ID NO:52) to VIIIb may constitute a protein with X and Y being major portions of the protein with the antigenic sequence being for example, part of an exposed loop on a globular protein.

It is preferred that if X or Y are present they are relatively short sequences, typically 1 to 3 residues long. In most instances X is preferably absent and Y is 1 or 2 residues long, e.g. -Cys or -Gly-Cys.

All the sequences herein are stated using the standard I.U.P.A.C. three-letter-code abbreviations for amino acid residues defined as follows: Gly-Glycine, Ala-Alanine, Val-Valine, Leu-Leucine, Ile-Isoleucine, Ser-Serine, Thr-Threonine, Asp-Aspartic acid, Glu-Glutamic acid, Asn-Asparagine, Gln-Glutamine, Lys-Lysine, His-Histidine, Arg-Arginine, Phe-Phenylalanine, Tyr-Tyrosine, Trp-Tryptophan, Cys-Cysteine, Met-Methionine and Pro-Proline.

Polypeptides according to the invention may be used to raise antibodies which will cross-react with prion proteins produced in a wide range of organisms. Our analyses have shown that since the conformational, topographic and electrostatic properties of polypeptides according to the invention are such that they are highly likely to elicit the production of antibodies which will cross-react with prion proteins from several or many organisms, further advantages may arise from combining several variant polypeptides in a larger polypeptide. Such a polypeptide may have the general formula (IX):

$$[L_a\text{-}F]_m\text{-}[L_b\text{-}G]_n\text{-}L_c \qquad (IX)$$

wherein F and G may each independently be a polypeptide or sub-fragment according to any one of Formulae I (SEQ ID NO:52) to VIIIb (SEQ ID NO:62), L is a linking sequence, a, b and c are each independently 0 or 1 and m and n are each positive numbers e.g. between 1 and 10 inclusive. L is preferably a short, conformationally flexible section of polypeptide chain such as, for example and without limit (Seq. I.D. No: 38) Gly-Gly-Gly-Gly-Gly, (Seq. I.D. No: 39) Gly-Pro-Gly-Pro-Gly-Pro or (Seq. I.D. No: 40) Gly-Ser-Ala-Gly-Ser-Gly-Ala. It should be clear that each repeat may optionally have a different variant of a polypeptide according to the invention.

It should be noted certain of the C-terminals correspond to N-terminals, particularly formula Va (SEQ ID NO:56) to formula Vb (SEQ ID NO:57), formula Vc (SEQ ID NO:58) to formula I (SEQ ID NO:52), formula I (SEQ ID NO:52) to formula II (SEQ ID NO:53), formula II (SEQ ID NO:53) to formula III (SEQ ID NO:54), formula III (SEQ ID NO:54) to formula VIIIa (SEQ ID NO:61) and formula VIIIb (SEQ ID NO:62) to formula IV (SEQ ID NO:55). Advantage may be taken to this correspondence when producing larger polypeptides according to formula IX. Linking sequences together with respective X and Y moieties may be omitted and residues in brackets may be selected so that either the regions of correspondence are duplicated or some or all of the duplicated residues are omitted. In the latter case it will be seen that the C-terminal of one polypeptide merges with the N-terminal of the other polypeptide.

Polyvalent determinant analogues as defined by Formula IX may be either what is referred to as pseudohomopolyvalent, wherein variants of essentially the same determinant analogue are repeated in a single polypeptide chain and/or heteropolyvalent, wherein distinct determinants are included in a single polypeptide. In addition, simple homopolyvalent polypeptide immunogens, which contain multiple copies of the same variant of one of the determinant analogues according to any one of formulae I (SEQ ID NO:52) to VIIIb (SEQ ID NO:62), would also be expected to be effective, and are also included within the scope of the present invention.

It is to be understood that any antigenically significant subfragments and/or antigenically significant variants of the above-identified polypeptide sequences which retain the general form and function of the parent polypeptide are included within the scope of this invention. In particular, the substitution of any of the specific residues by residues having comparable conformational and/or physical properties, including substitution by rare (but naturally occurring, e.g. D-stereoisomers) or synthetic amino acid analogues, is included. For example, substitution of a residue by another in the same Set, as defined below, is included within the ambit of the invention; Set 1 - Ala, Val, Leu, Ile, Phe, Tyr, Trp and Met; Set 2 - Ser, Thr, Asn and Gln; Set 3 - Asp and Glu; Set 4 - Lys, His and Arg; Set 5 - Asn and Asp; Set 6 - Glu and Gln; Set 7 - Gly, Ala, Pro, Ser and Thr. D-stereoisomers of all amino acid types, may be substituted, for example, D-Phe, D-Tyr and D-Trp.

In preferred embodiments of the invention, X and Y if present may independently include one or more segments of protein sequence with the ability to act as a T-cell epitope. For example, segments of amino acid sequence of the general formula 1-2-3-4, where 1 is Gly or a charged amino acid (e.g. Lys, His, Arg, Asp or Glu), 2 is a hydrophobic amino acid (e.g. Ile, Leu, Val, Met, Tyr, Phe, Trp, Ala), 3 is either a hydrophobic amino acid (as defined above) or an uncharged polar amino acid (e.g. Asn, Ser, Thr, Pro, Gln, Gly), and 4 is a polar amino acid (e.g. Lys, Arg, His, Glu, Asp, Asn, Gin, Ser, Thr, Pro), appear to act as T-cell epitopes in at least some instances (Rothbard, J. B. & Taylor, W. R. (1988). A sequence pattern in common to T-cell epitopes. The EMBO Journal 7(1): 93–100). Similarly segments can be of the sequence 1'-2'-3'-4'-5', wherein 1' is equivalent to 1 as defined earlier, 2' to 2, 3' and 4' to 3, and 5' to 4 (ibid).

Both forms are included within the scope of the present invention and one or more T-cell epitopes (preferably less than five) which may be of the type defined above or may be of other structure and which may be separated by spacer segments of any length or composition, preferably less than five amino acid residues in length and comprising for example residues selected from Gly, Ala, Pro, Asn, Thr, Ser or polyfunctional linkers such as non-α amino acids. It is possible for a C- or N-terminal linker to represent a complete protein, thus obviating the possible need for conjugation to a carrier protein.

Also included within the scope of this invention are derivatives of the polypeptides according to any one formulae I to VIIIb in which X or Y are or include a "retro-inverso" amino acid, i.e. a bifunctional amine having a functional group corresponding to an amino acid. For example an analogue according to the invention and containing a retro-inverso amino acid may have the formula:

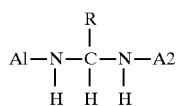

where R is any functional group, e.g. a glycine side chain, and A1 and A2 are preferably each a copy of one of the analogues defined herein (but not necessarily the same) attached by its N- or C-terminal end. T-cell epitopes may optionally be included as discussed earlier.

Retro-inverso modification of peptides involves the reversal of one or more peptide bonds to create analogues more resistant than the original molecule to enzymatic degradation and offer one convenient route to the generation of branched immunogens which contain a high concentration of epitope for a medium to large immunogen. The use of these compounds in large-scale solution synthesis of retro-inverso analogues of short-chain biologically active peptides has great potential.

Peptides according to the invention may be synthesised by standard peptide synthesis techniques, for example using either standard 9-fluorenylmethoxycarbonyl (F-Moc) chemistry (see, for example, Atherton, E. and Sheppard, R. C. (1985) J. Chem. Soc. Chem. Comm. 165) or standard butyloxycarbonate (T-Boc) chemistry although it is noted that, more recently, the fluorenylmethoxycarbonyl (Fmoc)/tert-butyl system, developed by Sheppard et al has found increasingly wide application (Sheppard, R. C.1986 Science Tools, The LKB Journal 33, 9). The correctness of the structure and the level of purity, which will normally be in excess of 85%, should be carefully checked, and particular attention be given to the correctness of internal disulphide bridging arrangements when present. Various chromatographic analyses, including high performance liquid chromatography, and spectrographic analyses, including Raman spectroscopy, may for example be employed for this purpose.

It is to be understood that the polypeptides according to the invention may be synthesised by any conventional method, either directly using manual or automated peptide synthesis techniques as mentioned above, or indirectly by RNA or DNA synthesis and conventional techniques of molecular biology and genetic engineering. Such techniques may be used to produce hybrid proteins containing one or more of the polypeptides inserted into another polypeptide sequence.

Another aspect of the present invention therefore provides a DNA molecule coding for at least one synthetic polypeptide according to the invention, preferably incorporated into a suitable expression vector replicable in microorganisms or in mammalian cells. The DNA may also be part of the DNA sequence for a longer product e.g. the polypeptides may be expressed as parts of other proteins into which they have been inserted by genetic engineering. One practical guide to such techniques is "Molecular cloning: a laboratory manual" by Sambrook, J., Fritsch, E. F. and Maniatis, T. (2nd Edition, 1989).

It should be noted that analogues incorporating retro-inverso amino acid derivatives cannot be made directly using a recombinant DNA system. However, the basic analogues can, and they can then be purified and chemically linked to the retro-inverso amino-acids using standard peptide/organic chemistry. A practical and convenient novel procedure for the solid-phase synthesis on polyamide-type resin of retro-inverso peptides has been described recently [Gazerro, H., Pinori, M. & Verdini, A. S. (1990). A new general procedure for the solid-phase synthesis of retro-inverso peptides. In "Innovation and Perspectives in Solid Phase Synthesis" Ed. Roger Epton. SPCC (UK) Ltd, Birmingham, UK].

The polypeptides are optionally linked to a carrier molecule, either through chemical groups within the polypeptides themselves or through additional amino acids added at either the C- or N-terminus, and which may be separated from the polypeptides themselves or surrounded by one or more additional amino acids, in order to render them optimal for their immunological function. Many linkages are suitable and include for example use of the side chains of Tyr, Cys and Lys residues. Suitable carriers include, for example, purified protein derivative of tuberculin (PPD), tetanus toxoid (TT), cholera toxin and its B subunit, ovalbumin, bovine serum albumin (BSA), soybean trypsin inhibitor (STI), muramyl dipeptide (MDP) and analogues thereof, diphtheria toxoid (DPT), keyhole limpet haemocyanin (KLH) and Braun's lipoprotein although other suitable carriers will be readily apparent to the skilled person. For example, multiple antigen peptides may be used such as those comprising a polylysyl core, e.g. heptalysyl, bearing reactive amine termini. Polypeptide antigens according to the invention may be reacted with, or synthesised on, the amino termini and different polypeptide antigens may be reacted with the same core or carrier. When using PPD as a carrier for polypeptides according to the invention, a higher titre of antibodies is achieved if the recipient of the polypeptide-PPD conjugate is already tuberculin sensitive, e.g. by virtue of earlier BCG vaccination. In the case of a human vaccine it is worth noting that in the UK and many other countries the population is routinely offered BCG vaccination and is therefore largely PPD-sensitive. Hence PPD is expected to be a preferred carrier for use in such countries.

The mode of coupling the polypeptide to the carrier will depend on the nature of the materials to be coupled. For example, a lysine residue in the carrier may be coupled to a C-terminal or other cysteine residue in a polypeptide by treatment with N-γ -maleimidobutyryloxy-succinimide (Kitagawa, T. & Ackawa, T. (1976) J. Biochem. 79, 233). Alternatively, a lysine residue in the carrier may be conjugated to a glutamic or aspartic acid residue in the peptide using isobutylchloroformate (Thorell, J. I. De Larson, S. M. (1978) Radioimmunoassay and related techniques: Methodology and clinical applications, p.288). Other coupling reactions and reagents have been described in the literature.

The polypeptides, either alone or linked to a carrier molecule, may be administered by any route (eg parenteral, nasal, oral, rectal, Intra-vaginal), with or without the use of conventional adjuvants (such as aluminium hydroxide or Freund's complete or incomplete adjuvants) and/or other immunopotentiating agents. The invention also includes formulation of polypeptides according to the invention in slow-release forms, such as a sub-dermal implant or depot comprising, for example, liposomes (Allison, A. C. & Gregoriadis, G. (1974) Nature (London) 252, 252) or biodegradable microcapsules manufactured from co-polymers of lactic acid and glycolic acids (Gresser, J. D. and Sanderson, J. E. (1984) in "Biopolymer Controlled Release Systems" pp 127–138, Ed. D. L. Wise).

Polypeptides according to the invention may be used either alone or linked to an appropriate carrier, as:
(a) As ligands in assays of, for example, serum from patients or animals;
(b) Peptide vaccines, for use in prophylaxis,
(c) As quality control agents in testing, for example, binding levels of antibodies raised against the polypeptides;
(d) As antigenic agents for the generation of monoclonal or polyclonal antibodies by immunisation of an appropriate animal, such antibodies being of use for (i) the scientific study of prion proteins, (ii) as diagnostic agents, e.g. as part of immunohistochemical reagents, (iii) for the passive immunisation of animals or patients, either as a treatment for encephalopathies or in combination with other agents, (iv) as a means of targeting other agents to regions comprising prion proteins, such agents either being linked covalently or otherwise associated, e.g. as in liposomes containing such agents and incorporating antibodies raised against any of the antigenic polypeptides and (v) for use as immunogens to raise anti-idiotype antibodies; such anti-idiotype antibodies also form part of this invention. The invention further provides for genetically engineered forms or sub-components, especially $V_H$ regions, of antibodies raised against the polypeptides, and of ovinised, bovinised, or humanised forms of antibodies initially raised against the polypeptides in other animals, using techniques described in the literature; and (e) The treatment of encephalopathies, either by displacing the binding of prion proteins to human or animal cells or by disturbing the three-dimensional organisation of the protein in vivo; as well as aiding the scientific study of prion proteins in vitro.

In respect of detection and diagnosis, of prion proteins or antibodies against prion proteins, the skilled person will be aware of a variety of immunoassay techniques known in the art, inter alia, sandwich assay, competitive and non-competitive assays and the use of direct and indirect labelling.

A further aspect of the invention provides a kit for detecting prion proteins or antibodies against prion proteins which comprises at least one synthetic polypeptide according to the invention.

The preparation of polyclonal or monoclonal antibodies, humanised forms of such antibodies (see, for example, Thompson K. M. et al (1986) Immunology 58, 157–160), single domain antibodies (see, for example, Ward, E. S., Gussow, D., Griffiths, A. D., Jones, P. and Winter, G. (1989) Nature 341, 544–546), and antibodies which might cross the blood-brain barrier, which bind specifically to a synthetic polypeptide according to the present invention, may be carried out by conventional means and such antibodies are considered to form part of this invention. Antibodies according to the invention are, inter alia, of use in a method of diagnosing mammalian encephalopathies which comprises incubating a sample of tissue or body fluid of mammal with an amount of antibody as described herein and determining whether, and if desired the extent to which and/or rate at which, cross-reaction between said sample and said antibody occurs. Diagnostic kits which contain at least one of said antibodies also form part of this invention.

A further aspect of the invention provides synthetic polypeptides for use in therapy or prophylaxis of mammalian encephalopathies and/or stimulating the mammalian immune system and/or blocking the cellular binding or aggregation of the prion proteins and for the preparation of medicaments suitable for such uses. Also included are pharmaceutical compositions containing, as active ingredient, at least one polypeptide or polypeptide-carrier conjugate as described herein in association with one or more pharmaceutically acceptable adjuvants, carriers and/or excipients. The compositions may be formulated for oral, rectal, nasal or especially parenteral administration (including intra-CNS administration).

The invention further provides a method of therapy or prophylaxis of mammalian encephalopathies and/or of stimulating the mammalian immune system and/or of blocking the cellular binding or aggregation of the prion proteins, which comprises administering an amount of a polypeptide as hereinbefore defined, either in isolation or in combination with other agents for the treatment of encephalopathies.

Discrimination between natural $PrP^C$ and $PrP^{SC}$ is highly desired since $PrP^C$ is found in normal subjects and both $PrP^C$ and $PrP^{SC}$ are found in a diseased subject. We have found that peptide sequences according to the invention, preferably those relating to regions A, B and C, and significant sub-fragments thereof may be used to discriminate between natural $PrP^C$ and infective $PrP^{SC}$. Also, antibodies raised against these peptide sequences and sub-fragments and the nucleotide sequences which code for such peptide sequences and sub-fragments may also be used to discriminate between $PrP^C$ and $PrP^{SC}$. Accordingly, the invention provides a method of discriminating between $PrP^C$ and $PrP^{SC}$ in which a sample is contacted with a substance selected from peptide sequences according to the invention, preferably those relating to regions A, B and C, and significant sub-fragments thereof, antibodies raised against said sequences and sub-fragments and the presence or absence of $PrP^{SC}$ is determined.

In some instances discrimination may be enhanced by pretreatment of the sample, for example by pre-digestion with enzymes e.g. proteinase K, or denaturation by strong alkali e.g. 6M guanidine hydrochloride or by a combination of such treatments.

It will be preferable to use the peptide sequences, antibodies and nucleotide sequences which relate to the specific subject under test, e.g. bovine sequences and antibodies for cattle, ovine sequences and antibodies for sheep.

It may be advantageous to immunise with a cocktail containing (i) a given analogue conjugated to more than one type of carrier molecule, and/or (ii) more than one kind of analogue conjugated to the same carrier molecule. Moreover, any of the peptide analogues, their conjugates, and cocktails thereof may be administered in any suitable adjuvant or delivery system, and more than one adjuvant or delivery system may be combined to form a so-called "super-cock-tail". Preferred adjuvants and delivery systems include aluminium hydroxide (alum), liposomes, micelles, niosomes, ISCOMS, Brauns lipoprotein and whole-cell or components of microbial animal vaccines.

EXAMPLE 1

A preferred bovine form of formula II (Seq. I.D. No: 41) Ala-Met-Ser-Arg-Pro-Leu-Ile-His-Phe-Gly-Ser-Asp-Tyr- Glu-Asp-Arg-Tyr-Tyr-Arg-Glu-Asn-Met-His-Arg-Gly-Cys (related to Seq. I.D. No: 7) in which the C-terminal Y extension is Gly-Cys according to the invention is synthesised using standard solid-phase Fmoc methodologies. The peptide is cleaved from the resin in the presence of trifluroacetic acid and subsequent purification is achieved by gel filtration, ion exhange chromatography and reverse phase high performance liquid chromatography. The peptide is conjugated to a variety of carriers by MBS (m-Maleimidobenzoyl-N-hydroxy succinimide ester), a well-known hetero-bifunctional reagent.

Examples of carriers include KLH, BSA and TT which have been shown to provide necessary immunopotentiating properties to B cell epitopes.

The peptide carrier conjugates are emulsified in Freund's Complete Adjuvant and are administered intramuscularly to mice. Subsequent booster injections are given in Freund's Incomplete Adjuvant.

The ensuing serum antibody response is monitored throughout the immunisation schedule by enzyme immunoassay (ELISA) using immobilised antigen (formula II), coupled to BSA, the serum sample under test, and an enzyme-labelled anti-mouse antibody.

In this example, use of carriers, adjuvants and delivery systems and booster injections are effected in order to determine an optimal protocol for producing anti-formula II antibodies.

EXAMPLE 2

Antibodies to formula II are used as diagnostic reagents for assaying the presence of prion protein in serum, in "cell carriers" in serum and in tissue biopsies of injected animal species.

A direct enzyme immunoassay (ELISA) can detect the presence of extracted prion protein by its immobilisation onto a solid substrate. Reaction of mouse antisera raised to formula II with native prion protein is detected with an enzyme-labelled anti-mouse antiserum. The reaction is quantified by addition of a suitable substrate and reading the optical density of the colour produced.

Furthermore, immunohistochemical diagnosis of prion proteins in tissue biopsies can be performed by reacting anti-formula II antibodies with paraffin wax embedded or frozen tissue. Reactions can be detected using a standard indirect immunoperoxidase technique.

EXAMPLE 3

MATERIALS AND METHODS

Peptide Synthesis

The following peptides were synthesised using standard solid-phase Fmoc methodologies.

Peptide II: (Seq. I.D. No: 42)

Ser—Ala—Met—Ser—Arg—Pro—Leu—Ile—His—Phe—
Gly—Asn—Asp—Tyr—Glu—Asp—Arg—Tyr—Tyr—
Gly—Cys (A preferred ovine sub-fragment of formula II).

Peptide BII: (Seq. I.D. No: 43)

Ser—Ala—Met—Ser—Arg—Pro—Leu—Ile—His—Phe—
Gly—Ser—Asp—Tyr—Glu—Asp—Arg—Tyr—Tyr—Gly—
Cys (A preferred bovine sub-fragment of formula II).

Peptide III: (Seq. I.D. No: 44)

Asn—Met—Tyr—Arg—Tyr—Pro—Asn—Gln—Val—Tyr—
Tyr—Arg—Pro—Val—Asp—Arg—Tyr—Ser—Asn—Gln—
Asn—Asn—Phe—Val—His—Gly—Cys (A preferred ovine sequence of formula III (p8, in 30–32).

Peptide BIII: (Seq. I.D. No: 45)

Asn—Met—His—Arg—Tyr—Pro—Asn—Gln—Val—Tyr—
Tyr—Arg—Pro—Val—Asp—Gln—Tyr—Ser—Asn—Gln—
Asn—Asn—Phe—Val—His—Gly—Cys (A preferred bovine sequence of formula III (p8, In 26–28).

Peptide Vb: (Seq. I.D. No: 46)

Gly—Gln—Pro—His—Gly—Gly—Gly—Trp—Gly—Gln—
Pro—His—Gly—Gly—Gly—Trp—Gly—Gln—Pro—His—
Gly—Gly—Gly—Trp—Gly—Cys (A preferred ovine/bovine sequence of formula Vb).

Peptide Vc: (Seq. I.D. No: 47)

Gly—Gln—Gly—Gly—Ser—His—Ser—Gln—Trp—Asn—
Lys—Pro—Ser—Lys—Pro—Lys—Thr—Asn—Met—Lys—
His—Val—Gly—Cys (A preferred ovine sequence of formula Vc).

Peptide VIIIb: (Seq. I.D. No: 48)

Cys—Ile—Thr—Gln—Tyr—Gln—Arg—Glu—
Ser—Gln—Ala—Tyr—Tyr—Gln—Arg (A preferred ovine/bovine sequence of formula VIIIb)

Peptide Va: (Seq. I.D. No: 49)

Gly—Gly—Trp—Asn—Thr—Gly—Gly—Ser—Arg—Tyr—
Pro—Gly—Gln—Gly—Ser—Pro—Gly—Gly—Asn—Arg—
Tyr—Pro—Pro—Gln—Gly—Gly—Gly—Cys

Peptide VIII(a: (Seq. I.D. No: 50)

Val—Asn—Ile—Thr—Val—Lys—Gln—His—Thr—Val—
Thr—Thr—Thr—Thr—Lys—Gly—Glu—Asn—Phe—Thr—
Glu—Gly—Cys (A preferred ovine sequence of formula VIIIa).

Peptide I: (Seq. I.D. No: 51)

Lys—His—Met—Ala—Gly—Ala—Ala—Ala—Ala—Gly—
Ala—Val—Val—Gly—Gly—Leu—Gly—Gly—Tyr—Met—
Leu—Gly—Ser—Ala—Met—Ser—Arg—Gly—Cys.

Peptides I, II, BII, III, BIII, Va, Vb, Vc and VIIIa were synthesised with the C-terminal extension according to the invention. The peptides were cleaved from the resin in the presence of trifluoroacetic acid and subsequent purification was achieved by reverse phase high performance liquid chromatography. All peptides had a purity of 85% or more.

Conjugation of peptides to ovalbumin

Peptides were conjugated through their C-terminal (peptides II, BII, III, BIII, Vb and Vc) or N-terminal (peptide VIIIb) Cys residues. Peptides were dissolved in dimethyl sulphoxide (DMSO) to a concentration of 10 mg/ml. Preactivated ovalbumin (Pierce, Imject Kit) was resuspended in 1 ml of distilled water, and equal volumes of preactivated ovalbumin and peptide were mixed and the solution allowed to stand at room temperature for 3 hours. The conjugate was dialysed overnight against phosphate buffered saline (PBS) to remove the DMSO and unconjugated peptide.

The extent of conjugation was determined by measuring the free-thiol content using an Ellman's assay and by monitoring the increase in the molecular mass of the conjugate by SDS-PAGE (sodium dodecyl sulphate-polyacrylamide gel electrophoresis).

Generation of rabbit antisera.

Antiserum was raised against each of the peptide conjugates in two female New Zealand White rabbits. Each rabbit received an amount of conjugate equivalent to 40 µg of peptide for both the primary inoculation and the boosters. Rabbits were injected as follows:

Day 0: Conjugate in Freund's Complete Adjuvant (1:1, v/v) intramuscularly.

Day 21: Conjugate in Freund's Incomplete Adjuvant (1:1, v/v) intramuscularly.

Day 31: Conjugate on its own intraperitoneally.

Animals were bled on day 41, and the sera assayed for anti-peptide antibody by ELISA (using free peptide as the coating antigen). The sera were also used in immunoblot and dot blot assays to see if they could recognise proteins from the brain homogenates.

Preparation of brain homogenates

Scrapie-free brain material was obtained from a flock of New Zealand sheep in quarantine.

Scrapie-infected brain material was obtained from a Department of Agriculture and had been histopathalogically diagnosed as being scrapie infected.

BSE-infected brain material was obtained via a government Agriculture Department and had been histopathalogically certified as being BSE infected.

BSE-free material was obtained through a private source.

Ha27–30 is brain material obtained from an inbred hamster scrapie model, which has been shown to cont Peptide II Good titres. Dot blots appear to indicate that some discrimination is occurring. Negative results were obtained from the Western blots.

Peptide III

Reasonable titres. Possibly there is recognition of a non-specific (perhaps non-protein) component in the proteinase K and guanidine treated samples. Negative results were obtained from the Western blots.

Peptide Vb

Good titres. Although it appears that there might be some discrimination occurring, the Vb peptide in fact occurs within the N-terminal region that is missing in $PrP^{SC}$. One would therefore not expect to see any recognition in the infected material treated with proteinase K and guanidine. However, one possible explanation is that the $PrP^C$ present in the infected material has not been completely digested by the proteinase K. Negative results were obtained from the Western blots.

Peptide Vc

Excellent titres. These results are exactly as expected. As mentioned previously, antibodies which recognise $PrP^{SC}$ generally only recognise the protein in its denatured state. Infected and uninfected samples, as well as containing $PrP^{SC}$ and/or $PrP^C$ in their "native" states, will also contain both PrP forms in various stages of denaturation due to natural protein turnover within cells. For this reason, antibodies would be expected to detect all three untreated samples. However, proteinase K treatment will digest $PrP^C$ and any partially denatured $PrP^{SC}$ leading to a loss of antibody recognition in all samples (assuming the antibody only recognises denatured PrP). The addition of guanidine should restore antibody recognition in material which had originally contained $PrP^{SC}$. Western blots showed up the expected protein bands at the correct molecular weights.

Peptide VIIIb

Reasonable titre. There may be recognition of a non-specific component. Negative results were obtained form the Western blots.

Peptides BII & BIII

The titres are reasonable and there are strong positive results from untreated normal and infected bovine brain material.

In summary, good anti-peptide titres obtained in all cases, the Western blots only worked well in the case of peptide Vc, which also gave the highest titre and the dot blots show that there is some discrimination occurring between $PrP^C$ and $PrP^{SC}$ with peptide Vc. Data from peptide II also suggests that discrimination is occurring.

TABLE I

Results from ovine peptide sequences

| Pept/ carrier ratio | Anti-body number | Titre | Ovine Brain Material | DOT BLOT Untrt | Prot K | Prot K + Gua | West Blot |
|---|---|---|---|---|---|---|---|
| II 8:1 | 93 | 20,000 | infected | ++ | + | + | |
| | | | normal | ++ | − | − | |
| | | | Ha27-30 | +/− | +/− | +/− | |
| II 8:1 | 94 | 20,000 | infected | ++ | + | + | |
| | | | normal | ++ | − | − | |
| | | | Ha27-30 | + | + | + | |
| III 6:1 | 101 | 5,000 | infected | ++ | + | + | |
| | | | normal | ++ | + | + | |
| | | | Ha27-30 | ++ | ++ | ++ | |

TABLE I-continued

Results from ovine peptide sequences

| Pept/ carrier ratio | Anti-body number | Titre | Ovine Brain Material | DOT BLOT Untrt | Prot K | Prot K + Gua | West Blot |
|---|---|---|---|---|---|---|---|
| III 6:1 | 102 | 5,000 | infected | +++ | + | + | |
| | | | normal | +++ | +/− | +/− | |
| | | | Ha27-30 | ++ | ++ | ++ | |
| Vc 5:1 | 97 | 160,000 | infected | +++ | +/− | +++ | + |
| | | | normal | +++ | +/− | +/− | + |
| | | | Ha27-30 | +++ | ++ | +++ | + |
| Vc 5:1 | 98 | 320,000 | infected | +++ | +/− | +++ | + |
| | | | normal | +++ | +/− | +/− | + |
| | | | Ha27-30 | +++ | +/− | +++ | + |

TABLE II

Results from ovine peptide sequences

| Pept/ carrier ratio | Anti-body number | Titre | Bovine Brain Material | DOT BLOT Untrt | Prot K | Prot K + Gua | West Blot |
|---|---|---|---|---|---|---|---|
| II 8:1 | 93 | 20,000 | infected | ++ | + | + | |
| | | | normal | ++ | + | + | |
| | | | Ha27-30 | +/− | +/− | +/− | |
| II 8:1 | 94 | 20,000 | infected | ++ | + | + | |
| | | | normal | ++ | + | + | |
| | | | Ha27-30 | + | + | + | |
| III 6:1 | 101 | 5,000 | infected | ++ | + | + | |
| | | | normal | ++ | + | + | |
| | | | Ha27-30 | ++ | ++ | ++ | |
| III 6:1 | 102 | 5,000 | infected | ++ | + | + | |
| | | | normal | ++ | + | + | |
| | | | Ha27-30 | ++ | ++ | ++ | |
| Vc 5:1 | 97 | 160,000 | infected | +++ | + | ++ | |
| | | | normal | ++ | + | + | |
| | | | Ha27-30 | +++ | ++ | +++ | |
| Vc 5:1 | 98 | 320,000 | infected | +++ | + | ++ | |
| | | | normal | ++ | +/− | +/− | |
| | | | Ha27-30 | +++ | +/− | +++ | |

TABLE III

Results from ovine/bovine peptide sequences

| Pept/ carrier ratio | Anti-body number | Titre | Ovine Brain Material | DOT BLOT Untrt | Prot K | Prot K + Gua | West Blot |
|---|---|---|---|---|---|---|---|
| Vb 6:1 | 95 | 50,000 | infected | ++ | + | + | |
| | | | normal | ++ | − | − | |
| | | | Ha27-30 | ++ | ++ | ++ | |
| Vb 6:1 | 96 | 10,000 | infected | ++ | + | + | |
| | | | normal | ++ | − | − | |
| | | | Ha27-30 | ++ | ++ | ++ | |
| VIIIb 12:1 | 103 | 3,000 | infected | ++ | + | + | |
| | | | normal | ++ | + | + | |

TABLE III-continued

Results from ovine/bovine peptide sequences

| Pept/carrier ratio | Antibody number | Titre | Ovine Brain Material | DOT BLOT Untrt | Prot K | Prot K + Gua | West Blot |
|---|---|---|---|---|---|---|---|
| | | | Ha27-30 | ++ | +/− | +/− | |
| VIIIb | 12:1 | 104 | 3,000 infected | + | + | + | |
| | | | normal | + | + | + | |
| | | | Ha27-30 | + | + | + | |

TABLE IV

Results from ovine/bovine peptide sequences

| Pept/carrier ratio | Antibody number | Titre | Bovine Brain Material | DOT BLOT Untrt | Prot K | Prot K + Gua | West Blot |
|---|---|---|---|---|---|---|---|
| Vb | 6:1 | 95 | 50,000 infected | ++ | + | + | |
| | | | normal | ++ | + | + | |
| | | | Ha27-30 | ++ | ++ | ++ | |
| Vb | 6:1 | 96 | 10,000 infected | ++ | + | + | |
| | | | normal | ++ | + | + | |
| | | | Ha27-30 | ++ | ++ | ++ | |
| VIIIb | 12:1 | 103 | 3,000 infected | ++ | + | + | |
| | | | normal | ++ | + | + | |
| | | | Ha27-30 | ++ | +/− | +/− | |
| VIIIb | 12:1 | 104 | 3,000 infected | + | + | + | |

TABLE IV-continued

Results from ovine/bovine peptide sequences

| Pept/carrier ratio | Antibody number | Titre | Bovine Brain Material | DOT BLOT Untrt | Prot K | Prot K + Gua | West Blot |
|---|---|---|---|---|---|---|---|
| | | | normal | ++ | +/− | +/− | |
| | | | Ha27-30 | + | + | + | |

TABLE V

Results from bovine peptide sequences

| Pept/carrier ratio | Antibody number | Titre | Bovine Brain Material | DOT BLOT Untrt | Prot K | Prot K + Gua | West Blot |
|---|---|---|---|---|---|---|---|
| BII | 9:1 | 105 | 100,000 infected | +++ | + | + | |
| | | | normal | +++ | + | + | |
| | | | Ha27-30 | + | + | + | |
| BII | 9:1 | 106 | 100,000 infected | +++ | + | + | |
| | | | normal | +++ | − | + | |
| | | | Ha27-30 | + | + | + | |
| BIII | 5:1 | 107 | 20,000 infected | +++ | +/− | +/− | |
| | | | normal | +++ | +/− | +/− | |
| | | | Ha27-30 | + | + | + | |
| BIII | 5:1 | 108 | 10,000 infected | +++ | +/− | +/− | |
| | | | normal | +++ | +/− | +/− | |
| | | | Ha27-30 | + | + | + | |

We claim:

1. A synthetic polypeptide having at least one antigenic site of a prion protein, wherein the polypeptide is a fragment of a prion protein and is selected from the group consisting of:

$$X-(Pro-Gly-Gly-R_{20})-Trp-Asn-Thr-Gly-Gly-Ser-$$
$$Arg-Tyr-Pro-Gly-Gln-Gly-Ser-Pro-Gly-Gly-Asn-$$

-continued $$Arg-Tyr-Pro-Pro-Gln-Gly-(Gly-R_{21}-R_{22}-Trp)-Y$$

(formula Va (SEQ ID NO:56));

$$X-(Gly-Gly-R_{21}-R_{22}-Trp)-Gly-Gln-Pro-His-$$
$$Gly-Gly-Gly-R_{23}-Trp(Gly-Gln-Pro-His)-Y$$

(formula Vb (SEQ ID NO:57));

-continued

X—(Gly—Gly—Gly—Trp)—Gly—Gln—Gly—Gly—R$_{24}$—R$_{25}$—

His—R$_{26}$—Gln—Trp—Asn—Lys—Pro—R$_{27}$—Lys—Pro—Lys—

Thr—R$_{28}$—R$_{29}$—Lys (—His—R$_{30}$—Ala—Gly)—Y (formula Vc (SEQ ID NO:58))

wherein R$_{20}$, R$_{21}$, R$_{23}$ and R$_{24}$ are each independently either Gly or absent;

R$_{22}$ either Gly or Thr;

R$_{25}$ is either Thr or Ser;

R$_{26}$ is an amino acid residue selected from Gly, Ser and Asn;

R$_{27}$ and R$_{28}$ are each independently either Asn or Ser;

R$_{29}$ is an amino acid residue selected from Met, Leu and Phe;

R$_{30}$ is either Val or Met, further wherein one or more residues within parentheses are present or absent with the proviso that if they are present they are attached to the rest of the peptide in sequence; and X and Y are each independently absent or independently are one or more additional amino acid residues, with the proviso that when present neither X nor Y provide or form part of an antigenic property of the prion protein which, in the corresponding portion of sequence of a natural prion protein, is contiguous with the sequence to which X and Y are attached; and

[L$_a$-F]$_m$-[L$_b$-G]$_n$-L$_c$    (formula IX)

wherein F and G are each independently a synthetic polypeptide comprising a fragment of a prion protein selected from the group consisting of Formulae Va, Vb and Vc; L is a linking sequence; a, b and c are each independently 0 or 1; and m and n are each positive numbers.

2. A synthetic polypeptide as claimed in claim 1 wherein at least one of the amino acid residues recited has been substituted by another amino acid residue which has comparable conformational or physical properties as the amino acid residue being substituted.

3. A synthetic polypeptide as claimed in claim 2 wherein said recited amino acid residue and said another amino acid residue are selected from one of the following sets of amino acid residues:

| | |
|---|---|
| Set 1 | Ala, Val, Leu, Ile, Phe, Tyr, Trp and Met; |
| Set 2 | Ser, Thr, Asn, and Gln; |
| Set 3 | Asp and Glu; |
| Set 4 | Lys, His and Arg; |
| Set 5 | Asn and Asp; |
| Set 6 | Glu and Gln; or |
| Set 7 | Gly, Ala, Pro, Ser, and Thr. |

4. A synthetic polypeptide as claimed in claim 2 wherein the substituted amino acid residue is a D-stereoisomer of the amino residue being substituted.

5. A synthetic polypeptide as claimed in claim 2 wherein the D-stereoisomer is selected from the group consisting of D-Phe, D-Tyr and D-Trp.

6. The synthetic polypeptide as claimed in claim 1 consisting of a sequence of general formula (IX):

[L$_a$-F]$_m$-[L$_b$-G]$_n$-L$_c$    (formula IX)

wherein F and G are each independently a synthetic polypeptide comprising a fragment of a prion protein selected from the group consisting of peptides of formulae Va (SEQ ID NO:56), Vb (SEQ ID NO:57), and Vc (SEQ ID NO:58); L is a linking sequence, a, b and c are each independently 0 or 1; and m and n are each positive numbers; or F and G are each independently a sub-fragment of a fragment of prion protein selected from the group consisting of formulae Va, Vb and Vc.

7. The synthetic polypeptide as claimed in claim 1 wherein said polypeptide is a fragment of a prion protein and is selected from the group consisting of Seq. I.D. No: 23
X—(Pro—Gly—Gly—Gly)—Trp—Asn—Thr—Gly—Gly—
Ser—Arg—Tyr—Pro—Gly—Gln—Gly—Ser—Pro—Gly—
Gly—Asn—Arg—Tyr—Pro—Pro—Gln—Gly—(Gly—
Gly—Gly—Trp)—Y;

Seq. I.D. No: 24
X—(Gly—Gly—Gly—Trp)—Gly—Gln—Pro—His—Gly—
Gly—Gly—Trp—(Gly—Gln—Pro—His)—Y;

Seq. I.D. No: 25
X—(Gly—Gly—Gly—Trp)—Gly—Gln—Gly—Gly—Thr—
His—Gly—Gln—Trp—Asn—Lys—Pro—Ser—Lys—Pro—
Lys—Thr—Asn—Met—Lys
(—His—Val—Ala—Gly)—Y;

Seq. I.D. No: 26
X—(Pro—Gly—Gly—Gly)—Trp—Asn—Thr—Gly—Gly—
Ser—Arg—Tyr—Pro—Gly—Gln—Gly—Ser—Pro—Gly—
Gly—Asn—Arg—Tyr—Pro—Pro—Gln—Gly—(Gly—Gly—
Gly—Trp)—Y;

Seq. I.D. No: 27
X—(Gly—Gly—Gly—Trp)—Gly—Gln—Pro—His—Gly—
Gly—Gly—Trp—(Gly—Gln—Pro—His)—Y;

Seq. I.D. No: 28
X—(Gly—Gly—Gly—Trp)—Gly—Gln—Gly—Gly—Ser—
His—Ser—Gln—Trp—Asn—Lys—Pro—Ser—Lys—Pro—
Lys—Thr—Asn—Met—Lys(—His—Val—Ala—Gly)—Y;

Seq. I.D. No: 29
X—Pro—Gly—Gly—Gly—Trp—Asn—Thr—Gly—Gly—
Ser—Arg—Tyr—Pro—Gly—Gln—Gly—Ser—Pro—Gly—
Gly—Asn—Arg—Tyr—Pro—Pro—Gln—Gly—(Gly—
Gly—Gly—Trp)—Y;

Seq. I.D. No: 30
X—(Gly—Gly—Gly—Trp)—Gly—Gln—Pro—His—Gly—
Gly—Gly—Trp—(Gly—Gln—Pro—His)—Y; and Seq. I.D. No: 31
X—(Gly—Gly—Gly—Trp)—Gly—Gln—Gly—Gly—Gly—
Thr—His—Ser—Gln—Trp—Asn—Lys—Pro—Ser—Lys—
Pro—Lys—Thr—Asn—Met—Lys
(—His—Met—Ala—Gly)—Y.

8. The synthetic polypeptide as claimed in claim 1 wherein said polypeptide is a fragment of a prion protein and is selected from Seq. I.D. No: 49
Gly—Gly—Trp—Asn—Thr—Gly—Gly—Ser—Arg—Tyr—
Pro—Gly—Gln—Gly—Ser—Pro—Gly—Gly—Asn—Arg—
Tyr—Pro—Pro—Gln—Gly—Gly—Cys:

Seq. I.D. No: 46
Gly—Gln—Pro—His—Gly—Gly—Gly—Trp—Gly—Gln—
Pro—His—Gly—Gly—Gly—Trp—Gly—Gln—Pro—His—
Gly—Gly—Gly—Trp—Gly—Cys; and Seq. I.D. No: 47
Gly—Gln—Gly—Gly—Ser—His—Ser—Gln—Trp—Asn—
Lys—Pro—Ser—Lys—Pro—Lys—Thr—Asn—Met—Lys—
His—Val—Gly—Cys.

9. The synthetic polypeptide which comprises an antigenically significant subfragment and/or antigenically significant variant of the polypeptide as claimed in claim 1.

10. The synthetic polypeptide as claimed in claim 1 wherein X and/or Y, when present, independently comprise a retro-inverso amino acid.

11. A DNA molecule which encodes for one synthetic polypeptide as claimed in claim 1.

12. A kit for detecting prion proteins or antibodies against prion proteins which comprises at least one synthetic polypeptide as claimed in claim 1.

13. A process for the manufacture of a synthetic polypeptide having at least one antigenic site of a prion protein, the process comprising the steps of coupling the residues using chemical, biological or recombinant techniques and isolating the polypeptide as defined in claim 1.

* * * * *

UNITED STATES PATENT AND TRADEMARK OFFICE
CERTIFICATE OF CORRECTION

PATENT NO. : 5,773,572

DATED : June 30, 1998

INVENTORS : Fishleigh et al.

It is certified that error appears in the above-identified patent and that said Letters Patent is hereby corrected as shown below:

Column 88, line 55: change "Tyr—Pro—Pro—Gln—Gly—Gly—Cys:" to --Tyr—Pro—Pro—Gln—Gly—Gly—Gly—Cys:--

Signed and Sealed this

Fifteenth Day of September, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,773,572

DATED : June 30, 1998

INVENTOR(S) : Robert V. Fishleigh et al.

It is certified that error appears in the above-identified patent and that said Letters Patent is hereby corrected as shown below:

In column 3, line 12 delete the comma between "$R_3$" and "is Ala".

In column 6, line 2, change "Asn-Met-His-Arg-Tyr-Pro-Asn-Val-Tyr-Tyr-" to -- Asn-Met-His-Arg-Tyr-Pro-Asn-Gln-Val-Tyr-Tyr- --

In column 7, line 9, change "X-(-$R_{14}$-$R_{15}$-Ser-$R_{16}$-$R_{17}$)-$R_{18}$-Leu-Phe-Ser-" to -- X-($R_{14}$-$R_{15}$-Ser--$R_{16}$-$R_{17}$)-$R_{18}$-Leu-Phe-Ser- --.

In column 7, line 23, change "X-(Gly-Ala-Ser-Val-)Ile-Leu-Phe-Ser-Ser-" to -- X-(Gly-Ala-Ser-Val)-Ile-Leu-Phe-Ser-Ser- --.

In column 7, line 39, change "Gly-Gly-Gly-$R_{23}$-Trp (Gly-Gln-Pro-His)-Y (Vb" to -- Gly-Gly-Gly-$R_{23}$-Trp-(Gly-Gln-Pro-His)-Y (Vb --.

In column 7, line 50, change "$R_{22}$ either Gly or Thr;" to -- $R_{22}$ is either Gly or Thr; --.

In column 8, line 35, change "X-Pro-Gly-Gly-Gly-Trp-Asn-Thr-Gly-Gly-" to -- X-(Pro-Gly-Gly-Gly)-Trp-Asn-Thr-Gly-Gly- --.

In column 21, line 38, change "form" to --from--.

In claim 1, column 86, line 64 change "Gly-Gly-Gly-$R_{23}$-Trp(Gly-Glu-Pro-His)-Y" to -- Gly-Gly-Gly-$R_{23}$-Trp-(Gly-Glu-Pro-His)-Y --.

In claim 1, column 87, line 11, change "$R_{22}$ either Gly or Thr;" to -- $R_{22}$ is either Gly or Thr; --.

In claim 7, column 88, line 36, change "X-Pro-Gly-Gly-Gly-Trp-Asn-Thr-Gly-Gly-" to -- X-(Pro-Gly-Gly-Gly)-Trp-Asn-Thr-Gly-Gly- --.

UNITED STATES PATENT AND TRADEMARK OFFICE
CERTIFICATE OF CORRECTION

PATENT NO. : 5,773,572

DATED : June 30, 1998

INVENTORS : Fishleigh et al.

It is certified that error appears in the above-identified patent and that said Letters Patent is hereby corrected as shown below:

Column 88, line 55: change "Tyr—Pro—Pro—Gln—Gly—Gly—Cys:" to --Tyr—Pro—Pro—Gln—Gly—Gly—Gly—Cys:--

Signed and Sealed this

Fifteenth Day of May, 2001

*Attest:*

NICHOLAS P. GODICI

*Attesting Officer*  *Acting Director of the United States Patent and Trademark Office*